(12) United States Patent
Drake et al.

(10) Patent No.: US 11,478,962 B2
(45) Date of Patent: Oct. 25, 2022

(54) METHOD OF MANUFACTURING ELASTOMER ARTICLES HAVING EMBEDDED ELECTRONICS

(71) Applicant: West Pharmaceutical Services, Inc., Exton, PA (US)

(72) Inventors: Kerry Drake, Red Hill, PA (US); Heike Gruen, Aachen (DE); Jeffrey M. Laubach, Emmaus, PA (US); Martin McGarry, Dublin (IE); Jason Krizan, Elkton, MD (US); Patrick Dowling, Dublin (IE); Joel Worman, Palm Harbor, FL (US)

(73) Assignee: West Pharmaceutical Services, Inc., Exton, PA (US)

( * ) Notice: Subject to any disclaimer, the term of this patent is extended or adjusted under 35 U.S.C. 154(b) by 113 days.

(21) Appl. No.: 16/618,945

(22) PCT Filed: Jun. 6, 2018

(86) PCT No.: PCT/US2018/036191
§ 371 (c)(1),
(2) Date: Dec. 3, 2019

(87) PCT Pub. No.: WO2018/226780
PCT Pub. Date: Dec. 13, 2018

(65) Prior Publication Data
US 2021/0086410 A1    Mar. 25, 2021

Related U.S. Application Data

(60) Provisional application No. 62/515,623, filed on Jun. 6, 2017, provisional application No. 62/515,694, filed on Jun. 6, 2017.

(51) Int. Cl.
*B29C 43/18* (2006.01)
*B29C 43/36* (2006.01)
(Continued)

(52) U.S. Cl.
CPC ............. *B29C 43/18* (2013.01); *A61J 1/1468* (2015.05); *B29B 13/04* (2013.01); *B29C 43/003* (2013.01);
(Continued)

(58) Field of Classification Search
CPC ..... B29C 43/18; B29C 43/20; B29C 2043/18; B29C 70/685; B29C 70/70
See application file for complete search history.

(56) References Cited

U.S. PATENT DOCUMENTS 2,451,913 A * 10/1948 Brice ................. B29C 70/70
428/67
3,350,252 A * 10/1967 Twickler ............ A63B 37/0001
156/228
(Continued)

FOREIGN PATENT DOCUMENTS

CN     103702701 A    4/2014
CN     106018230 A    10/2016
(Continued)

OTHER PUBLICATIONS

Fassler, Andrew, and Carmel Majidi. "3D structures of liquid-phase Gain alloy embedded in PDMS with freeze casting." Lab on a Chip 13.22 (Sep. 5, 2013): 4442-4450. (Year: 2013).*
(Continued)

*Primary Examiner* — Benjamin A Schiffman
(74) *Attorney, Agent, or Firm* — Blank Rome LLP

(57) ABSTRACT

A method of manufacturing a medical component includes preparing a first sheet of an elastomeric material, arranging at least one electronic device in the first sheet of elastomeric material to obtain an elastomeric preform, and arranging the elastomeric preform in a mold and molding the elastomeric
(Continued)

preform therein to cure the elastomeric material and form the medical component having the at least one electronic device embedded therein.

14 Claims, 19 Drawing Sheets

(51) Int. Cl.

| | | |
|---|---|---|
| *B29B 13/04* | (2006.01) | |
| *B29C 67/00* | (2017.01) | |
| *B29C 43/58* | (2006.01) | |
| *A61J 1/14* | (2006.01) | |
| *B29C 43/00* | (2006.01) | |
| *B29L 31/34* | (2006.01) | |
| *B29L 31/00* | (2006.01) | |
| *B29K 23/00* | (2006.01) | |
| *A61K 38/28* | (2006.01) | |

(52) U.S. Cl.
CPC .............. *B29C 43/36* (2013.01); *B29C 43/58* (2013.01); *B29C 67/0018* (2013.01); *A61K 38/28* (2013.01); *B29C 2043/182* (2013.01); *B29C 2043/3602* (2013.01); *B29C 2043/5808* (2013.01); *B29C 2043/5816* (2013.01); *B29K 2023/22* (2013.01); *B29L 2031/3481* (2013.01); *B29L 2031/753* (2013.01)

(56) References Cited

U.S. PATENT DOCUMENTS

| | | | | |
|---|---|---|---|---|
| 4,248,818 | A * | 2/1981 | Elizabeth | B29C 43/02 264/107 |
| 5,808,203 | A | 9/1998 | Nolan et al. | |
| 5,955,021 | A * | 9/1999 | Tiffany, III | G06K 19/07745 264/272.11 |
| 6,105,248 | A * | 8/2000 | Tani | B29C 43/18 156/245 |
| 6,693,441 | B2 * | 2/2004 | Lane | G06V 40/1306 427/7 |
| 6,743,202 | B2 * | 6/2004 | Hirschman | A61M 5/14546 604/131 |
| 6,837,021 | B2 * | 1/2005 | Sudo | B29C 43/18 49/501 |
| 7,195,609 | B2 * | 3/2007 | Huegli | A61M 5/31513 604/181 |
| 8,282,013 | B2 * | 10/2012 | Stewart | F16J 15/108 235/492 |
| 8,773,660 | B2 * | 7/2014 | Pommereau | A61M 5/14566 356/343 |
| 9,413,061 | B2 * | 8/2016 | Battocchio | B60C 23/0493 |
| 9,855,389 | B2 * | 1/2018 | Pommereau | A61J 1/06 |
| 10,076,609 | B2 * | 9/2018 | Ashby | A61M 5/31513 |
| 10,082,830 | B2 * | 9/2018 | Lettow | G06F 1/163 |
| 10,096,896 | B2 * | 10/2018 | Mueller | H01Q 1/50 |
| 10,704,944 | B2 * | 7/2020 | Searle | G01F 11/027 |
| 2001/0034506 | A1 | 10/2001 | Hirschman et al. | |
| 2003/0233075 | A1 | 12/2003 | Huegli | |
| 2004/0083666 | A1 * | 5/2004 | Sudo | B29C 43/38 52/309.7 |
| 2007/0069418 | A1 | 3/2007 | Liao et al. | |
| 2009/0005729 | A1 | 1/2009 | Hendrixson et al. | |
| 2011/0009925 | A1 | 1/2011 | Leigh et al. | |
| 2011/0240747 | A1 | 10/2011 | Stewart et al. | |
| 2012/0195182 | A1 | 8/2012 | Pommereau et al. | |
| 2014/0333492 | A1 | 11/2014 | Battocchio | |
| 2015/0217059 | A1 | 8/2015 | Ashby et al. | |
| 2016/0074587 | A1 | 3/2016 | Searle et al. | |
| 2016/0151558 | A1 | 6/2016 | Tobescu | |
| 2016/0259913 | A1 | 9/2016 | Yu et al. | |
| 2017/0005406 | A1 * | 1/2017 | Mueller | H01Q 1/50 |
| 2017/0082456 | A1 | 3/2017 | Sakate et al. | |
| 2017/0312430 | A1 | 11/2017 | Schleicher et al. | |
| 2018/0193567 | A1 | 7/2018 | Schleicher et al. | |
| 2021/0121635 | A1 * | 4/2021 | Drake | A61M 5/24 |
| 2021/0308382 | A1 * | 10/2021 | Krizan | A61M 5/31513 |

FOREIGN PATENT DOCUMENTS

| | | |
|---|---|---|
| CN | 106062448 A | 10/2016 |
| EP | 1908487 A1 | 4/2008 |
| ES | 2381945 A1 | 6/2012 |
| JP | S5566365 A | 5/1980 |
| JP | 2002518108 A | 6/2002 |
| JP | 2013505433 A | 2/2013 |
| JP | 2015179829 A | 10/2015 |
| WO | 9965548 A1 | 12/1999 |
| WO | 2004086492 A1 | 10/2004 |
| WO | 2011032956 A2 | 3/2011 |
| WO | 2015103563 A1 | 7/2015 |
| WO | 2015139962 A1 | 9/2015 |
| WO | 2018/226780 A1 | 12/2018 |

OTHER PUBLICATIONS

Int'l Search Report and Written Opinion dated Oct. 15, 2018 in Int'l Application No. PCT/US2018/036191.
Third Party Submission issued Feb. 5, 2021 in European Application No. 18734390.0.
Office Action dated Mar. 2, 2021 in Japanese Application No. 2019-566867.
Office Action dated Apr. 1, 2021 in Chinese Application No. 20188037372.8.
Office Action dated May 8, 2021 in Chinese Application No. 201880037373.2.
Office Action dated Jun. 3, 2021 in Indian Application No. 201927051080.
Office Action dated Jun. 15, 2021 in Japanese Application No. 2019-566865.
Int'l Preliminary Report on Patentability dated Oct. 15, 2019 in Int'l Application No. PCT/US2018/036194.
Int'l Search Report and Writtien Opinion dated Sep. 12, 2018 in Int'l Application No. PCT/US2018/036194.

\* cited by examiner

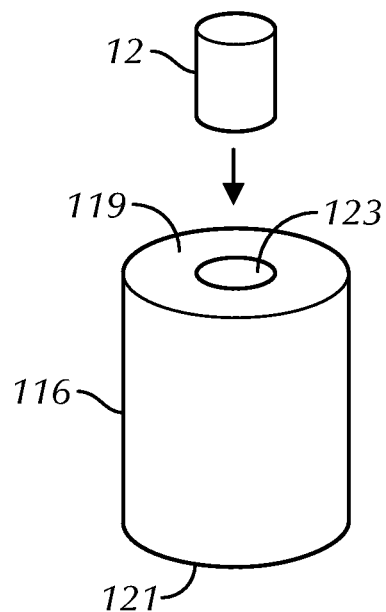
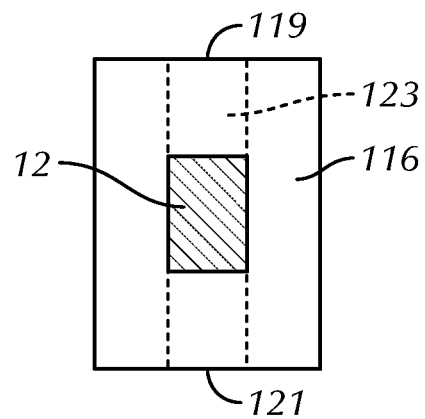
FIG. 3A          FIG. 3B
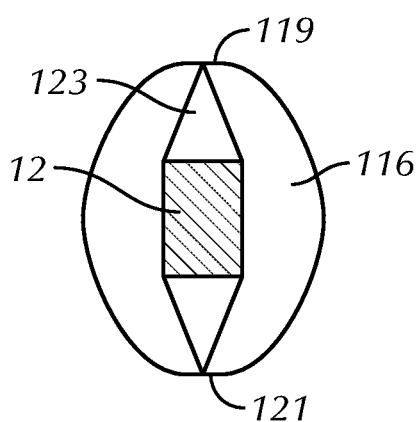
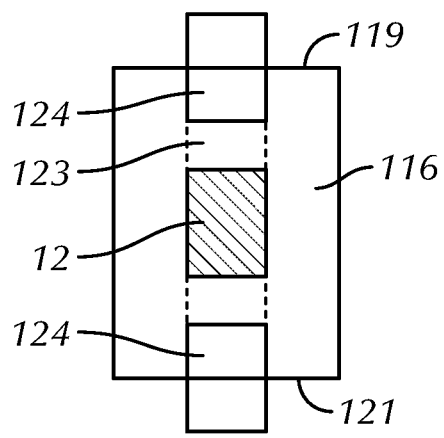
FIG. 3C          FIG. 3D

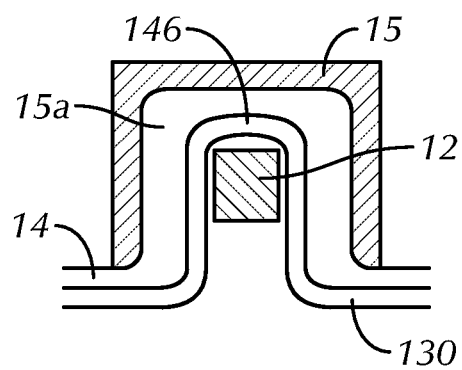
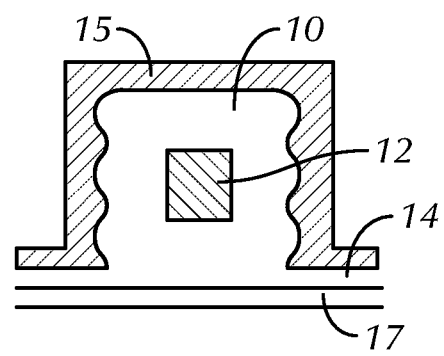
FIG. 11A  FIG. 11B
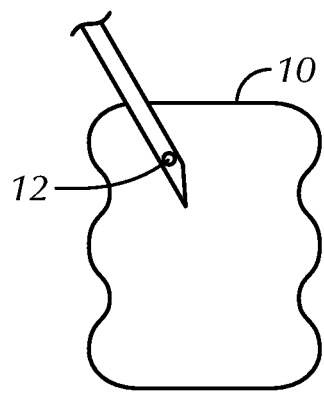
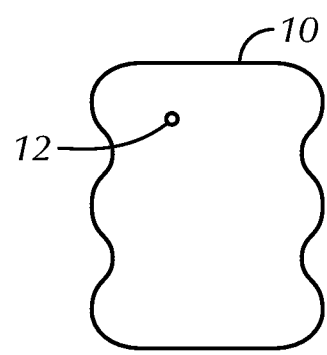
FIG. 12A  FIG. 12B

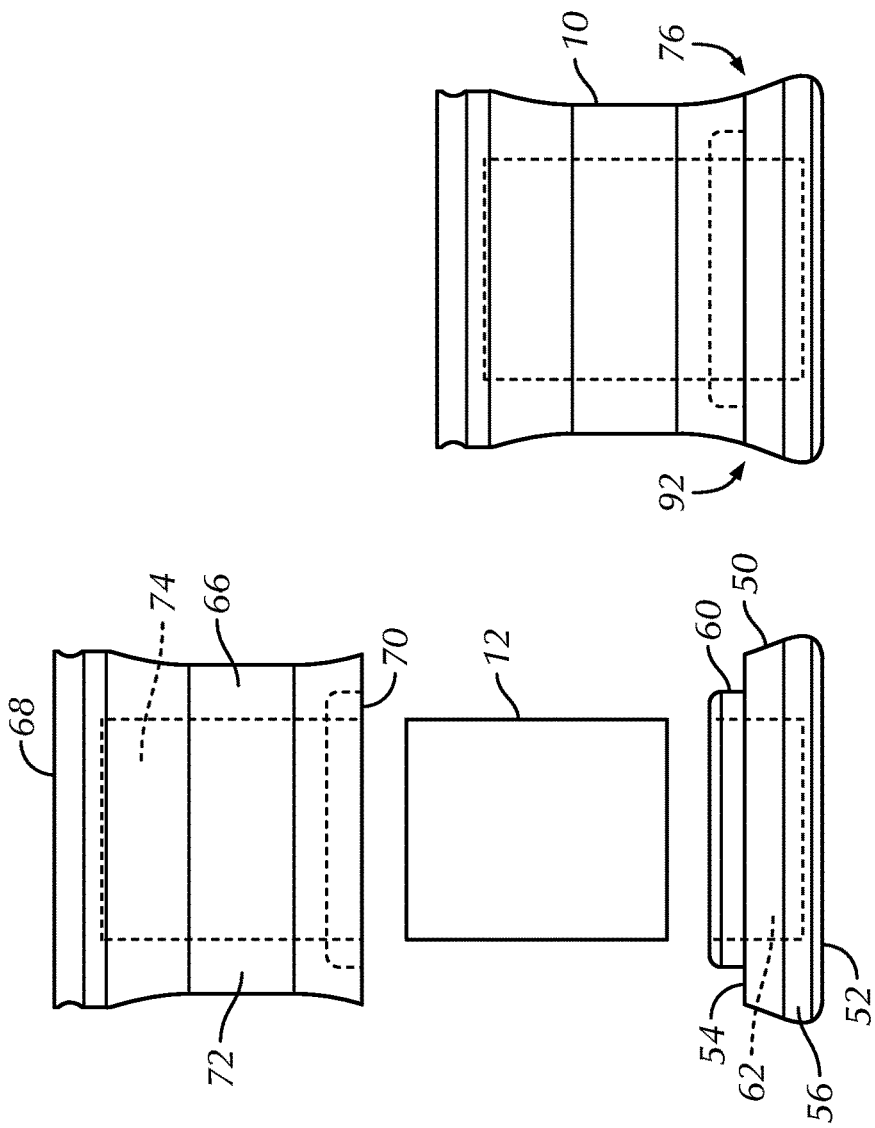

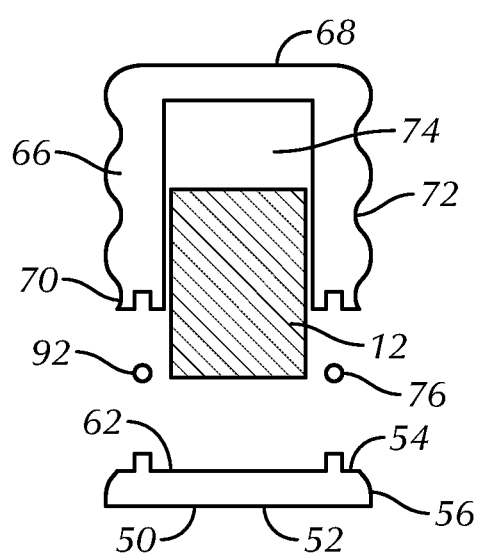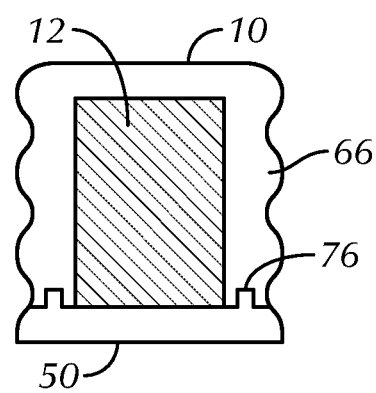
*FIG. 20A*  *FIG. 20B*

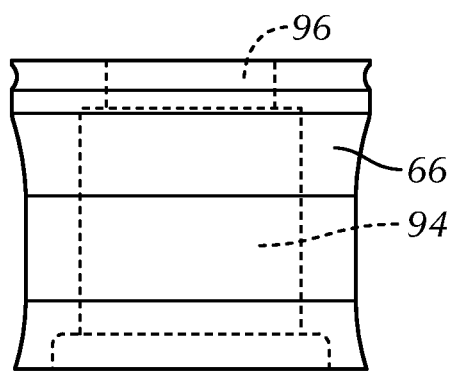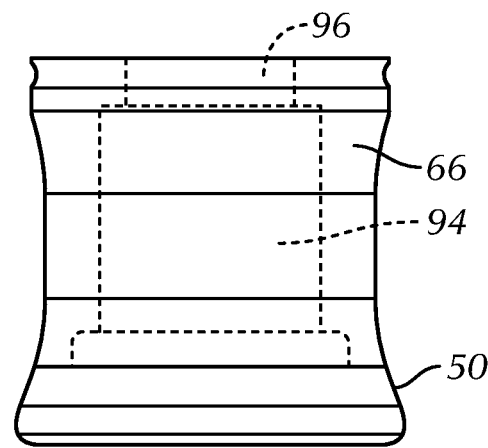
FIG. 21A  FIG. 21B
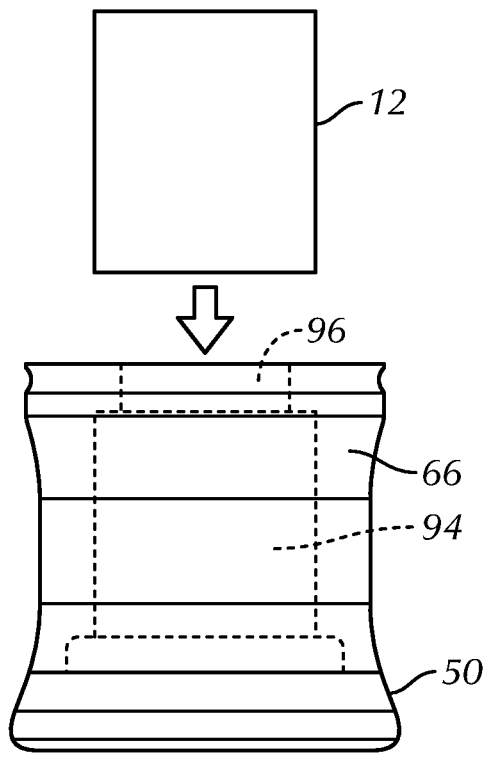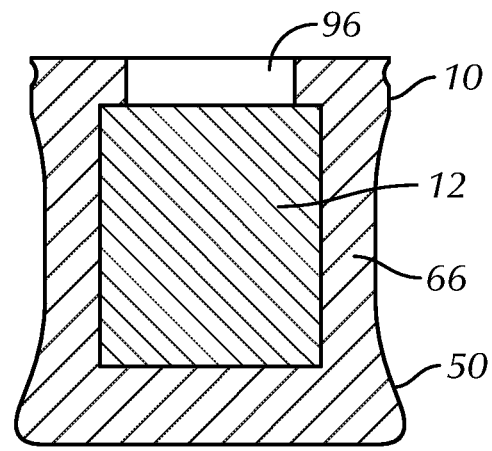
FIG. 21C  FIG. 21D

METHOD OF MANUFACTURING ELASTOMER ARTICLES HAVING EMBEDDED ELECTRONICS

CROSS-REFERENCE TO RELATED APPLICATIONS

This application is a section 371 of International Application No. PCT/US2018/036191, filed Jun. 6, 2018, which was published on Dec. 13, 2018 under International Publication No. WO 2018/226780 A1, and which claims priority from U.S. Provisional Patent Application Nos. 62/515,623 and 62/515,694, both filed Jun. 6, 2017, the disclosures of which are herein incorporated by reference.

BACKGROUND OF THE INVENTION

The present invention relates generally to elastomer articles having electronics embedded therein and, more particularly, to molded elastomer articles having one or more embedded electronic devices.

It is desirable to enable drug delivery devices to communicate an operational status of the device (e.g., pre-use and/or dosage complete conditions), identification information, other conditions (e.g., ambient temperature), and the like to enable monitoring of a patient or for like purposes. Such devices are known as "smart" devices.

Conventional "smart" devices tend to comprise multiple parts of at least two different materials. For example, one known syringe plunger device is formed of two pieces, one piece being formed of an elastomeric material and another piece being formed of a different plastic or elastomeric material, with an electronic circuit at the interface between the two plunger pieces. Other conventional "smart" devices include conventional electronic components, including sensors, in plungers, where the electronic components are encapsulated in a first component formed of first elastomeric material formable at lower temperatures that the electronic components can withstand, and then the formed first component is encapsulated in a second elastomeric material, to form the plunger. That is, the prior art smart plungers are three-piece plungers.

The present invention provides new and improved methods of manufacturing elastomer articles with embedded electronics for pharmaceutical containment. For example, embodiments of the methods of the present invention avoid heat damage to the sensitive electronics and ensure complete encapsulation and protection of the sensitive electronics from operational environmental conditions. The methods of the present invention also allow for greater control in how the electronics are positioned and can better work around the requirements of the electronics.

BRIEF SUMMARY OF THE INVENTION

The present invention relates to methods of manufacturing a component, such as a piston, plunger, closure or stopper, of a medical device, such as a cartridge, syringe or vial, comprising a molded elastomeric body and at least one electronic device embedded within and fully encapsulated by the elastomeric material of the component.

One preferred embodiment of the present invention is directed to a method of manufacturing a medical component. The method includes preparing a first sheet of an elastomeric material, arranging at least one electronic device in the first sheet of elastomeric material to obtain an elastomeric preform, and arranging the elastomeric preform in a mold and molding the elastomeric preform therein to cure the elastomeric material and form the medical component having the at least one electronic device embedded therein.

Another preferred embodiment of the present invention relates to a method of manufacturing a medical component. The method includes preparing a tube of an uncured or a partially cured elastomeric material. The tube has a first end, an opposing second end and a hollow interior extending between the first and second ends. The method further includes arranging at least one electronic device in the hollow interior to obtain a elastomeric preform, and subjecting the elastomeric preform to a molding process selected from the group consisting of compression molding, bladder molding and thermoforming in order to cure the elastomeric material and form the medical component having the at least one electronic device embedded therein.

Another preferred embodiment of the present invention is directed to a method of manufacturing a medical component. The method includes molding a form of an elastomeric material. The form has an inverted shape of the medical component to be formed. The method further includes arranging at least one electronic device to be in contact with the form, and inverting the form over the at least one electronic device to form the medical component having the at least one electronic device embedded therein.

Another preferred embodiment of the present invention is directed to a method of manufacturing a medical component including molding the medical component from an elastomeric material using one or more molding processes, and inserting at least one electronic device into a body of the molded medical component.

Another preferred embodiment of the present invention is directed to a method of manufacturing a medical component including molding a first member of the medical component from an elastomeric material. The first member includes a first end defined by a closed base wall, an opposing second end which is an open end, a sidewall extending between the first and second ends, and an internal recess configured to receive a portion of at least one electronic device. The method further includes positioning the at least one electronic device within the recess of the first member to form an assembly, and overmolding the assembly with the elastomeric material to form the medical component having the at least one electronic device embedded therein.

Another preferred embodiment of the present invention is directed to a component for a container to be filled with a pharmaceutical medicament. The component includes a unitary body formed of an elastomeric material and at least one electronic device embedded within the unitary body and encapsulated by the elastomeric material, wherein the unitary body is configured to contact an interior surface of the container.

Another preferred embodiment of the present invention is directed to a component for a container to be filled with a pharmaceutical medicament. The component includes a unitary body formed of an elastomeric material and at least one magnetic material embedded within the unitary body and encapsulated by the elastomeric material, wherein the unitary body is configured to contact an interior surface of the container.

Another preferred embodiment of the present invention is directed to a container containing insulin or a derivative, formulation or analog thereof and a component. The component is made of an elastomeric material and includes at least one electronic device or at least one magnetic material embedded therein.

Advantageous refinements of the invention are specified in the dependent claims. These refinements can be implemented alone or in any combination with each other.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIGS. 3A-3H schematically illustrate a method of manufacturing a medical component in a one-step molding process according to another preferred embodiment of the present invention;

FIGS. 11A-11B schematically illustrate a method of manufacturing a medical component in a one-step molding process according to a further preferred embodiment of the present invention;

FIGS. 12A-12B schematically illustrate a method of manufacturing a medical component in a one-step molding process according to another preferred embodiment of the present invention;

FIGS. 19A-19C illustrate a method of manufacturing a medical component in a two-step molding process according to another preferred embodiment of the present invention;

FIGS. 20A-20B are cross-sectional views of a portion of the component manufactured by the method illustrated in FIGS. 19A-19C;

FIGS. 21A-21D illustrate a method of manufacturing a medical component in a two-step molding process according to another preferred embodiment of the present invention;

DETAILED DESCRIPTION OF THE INVENTION

Figure 1A:
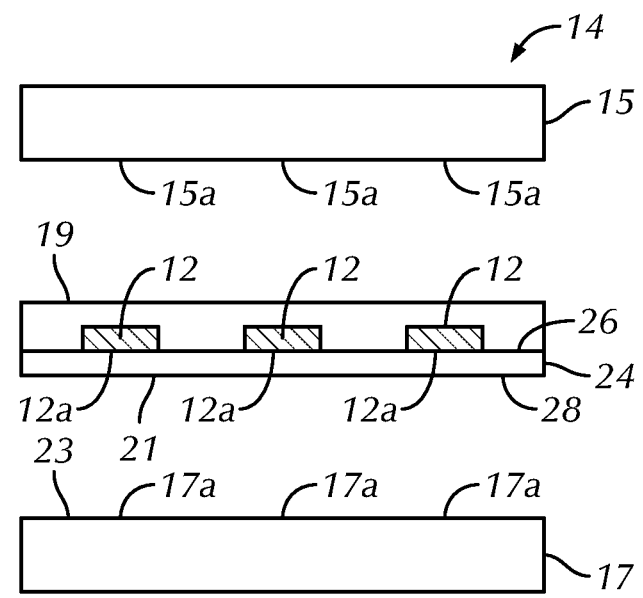
FIGS. 1A-1B illustrate a method of manufacturing a medical component in a one-step molding process according to a preferred embodiment of the present invention.

Certain terminology is used in the following description for convenience only and is not limiting. The words "proximal," "distal," "upward," "downward," "bottom" and "top" designate directions in the drawings to which reference is made. The words "inwardly" and "outwardly" refer to directions toward and away from, respectively, a geometric center of the device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIGS. 1A-23B show preferred embodiments of a component 10 of a medical device provided with an electronic device 12 embedded therein and methods of manufacturing such a medical device component 10. The medical device component 10 is hereinafter referred to as "medical component" for the sake of brevity. It will be understood that the medical component 10 may be utilized in any known medical device, and more particularly in any container having a cavity or a chamber capable of being filled with a substance. For example, the container may be, without limitation, a syringe, a cartridge, a vial and the like. More particularly, the medical device may be a cartridge, a syringe with needles, a needleless syringe, an inhaler, a solid dosage dispenser, a pen-type injector, an autoinjector, a wearable injector, a vial and the like.

It will be understood by those skilled in the art that the term piston may be used interchangeably herein with the term plunger, stopper, closure and the like.

The medical component 10 is preferably made of a polymeric material, and more preferably of an elastomeric material. In a preferred embodiment, the elastomeric material is either a thermoset elastomer or a thermoplastic elastomer (TPE). For example, the elastomeric material used for the elastomeric closure can be, for example, a synthetic or natural rubber, such as butyl rubber, isoprene rubber, butadiene rubber, halogenated butyl rubber (e.g., bromobutyl rubber), ethylene propylene terpolymer, silicone rubber, combinations thereof and the like. Preferably, the elastomeric material is a butyl or halobutyl elastomer.

The medical component 10 can be, for example, a cartridge piston (plunger, stopper or closure), a syringe piston (plunger, stopper or closure), a vial piston (plunger, stopper or closure), a seal, a gasket, a component of a pre-filled syringe, a sleeve or container stopper, a flashback bulb, a cap, a liner, a washer, or any other component/device which may be in contact with pharmaceutically pure materials or medicament. In a preferred embodiment, the pharmaceutical medicament with which the medical component 10 may be used is insulin (or any derivative, formulation or analog thereof). For example, as used herein, the term "insulin" shall mean insulin, insulin analogs, insulin derivatives or mixtures thereof, including human insulin or a human insulin analogs or derivatives. Examples of insulin analogs include, but are not limited to, Gly(A21), Arg(B31), Arg (B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives include, but are not limited to, B29-N-myristoyl-des(B30) human insulin; B29-N-palmitoyl-des(B30) human insulin; B29-N-myristoyl human insulin; B29-Npalmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N (N-palmitoyl-Y-glutamyl)-des(B30) human insulin; B29-N (N-lithocholyl-Y-glutamyl)-des(B30) human insulin; B29-N-(w-carboxyheptadecanoyl)-des(B30) human insulin and B29-N-(w-carboxyheptadecanoyl) human insulin.

For some diabetics, in particular, dosages frequently change and need to be calculated based on meals, time, and formulation. A patient may thus have to juggle multiple daily injections of insulin, such as quick-release (meal-time) insulin or long-acting (once-daily) insulin. The smart device of the present invention facilitates calculating dosages, tracking dosages (i.e., which drug, amount and time) and preventing accidental over/under doses. Improved integration of insulin treatments can therefore clearly help minimize the impact of diabetes on the patient and assist caregivers with feedback to better manage treatment. Such dosage calculation/tracking features are also useful for many other types of pharmaceutical medicaments and many other types of illnesses or conditions, such as, but not limited to multiple sclerosis and arthritis. The smart device of the present invention is especially pertinent for biologic drugs/enzymes for, for example, monitoring of transport conditions (e.g., ensuring that the cold chain and/or dark storage was maintained for efficacy of the drug), because these types of drugs are significantly less stable than many other drugs, and thus would benefit from "smart" technology to ensure consistency and patient safety. However, it will be understood that the medical component 10 may be used with any known or yet to be developed pharmaceutical medicament.

For brevity, the present invention is generally described herein with reference to a syringe piston or plunger tip.

The electronic device 12 may comprise any known electronic circuitry, electronic coding, microprocessor, sensor and the like. For example, the electronic device 12 may comprise one or more of an integrated circuit (or electronic chip or microchip), a radio-frequency identification (RFID) chip/coil/antenna and supporting components, a near-field communication (NFC) chip, an EEPROM chip, a solid state memory, a muscle wire, a piezoelectric sensor or actuator, a thermal sensor (e.g., a thermistor or a PTC thermistor), a pressure sensor, a level sensor, a dosage sensor, a mechanical sensor, an electromagnetic sensor, an optical sensor, a pneumatic sensor, a hydraulic sensor, a photosensitive sensor, a flow sensor, a power supply (e.g., a RF induction coil, a miniature coin battery, a super capacitor), a haptic feedback device (e.g., an LED or piezoelectric device) and the like. The electronic device 12 may be further equipped with a communication unit, preferably with a wireless communication unit by way of which the content of stored data can be retrieved on demand. For example, the electronic device 12 may comprise a RFID element enabling communication with a corresponding reading device in a wireless manner. This way, counterfeited medical components can be easily detected.

For all of the embodiments disclosed herein, the time, heat and pressure for each molding step will depend upon various factors, such as the specific elastomeric material being used and whether the desired result is partial curing of the elastomeric material or full curing of the elastomeric material. Such elastomeric materials and molding processes (e.g., compression molding, injection molding, overmolding, and the like) are well known in the art and a detailed description of each molding step time, temperature and pressure specifications is not necessary for a complete understanding of the present invention. For example, each molding step for the embodiments disclosed herein is conducted preferably at temperatures of about 120 to 310° C. and pressures of about 40 to 350 kg/cm$^2$ for a few seconds (e.g., less than 10 seconds) to 30 minutes, and more preferably about 120 to 220° C. and pressures of about 40 to 70 kg/cm$^2$ for about 30 seconds to 30 minutes, and most preferably at temperatures of about 140 to 220° C. and pressures of about 40 to 70 kg/cm$^2$ for about 2 to 15 minutes.

It will be understood by those skilled in the art that, for thermally sensitive devices, the medical component 10 may be molded so that there is only partial curing. Subsequently, the component 10 may be post cured as necessary by a secondary process, such as oven postcure, microwave curing, ebeam curing and the like. For example, post curing processes may be carried out at temperatures of about 120 to 310° C. and for up to 24 hours.

Referring to FIGS. 1A-2E, there are shown various embodiments of methods of manufacturing the medical component 10 utilizing a mold 14 and an elastomer sheet 16 in a one-step molding process, and more particularly in a one-step compression molding process. The mold 14 includes an upper mold half 15 having an open cavity 15a and a lower mold half 17 having an open cavity 17a. Each cavity 15a, 17a is preferably an open heated mold cavity 15. In a preferred embodiment, the mold 14 includes a plurality of upper and lower mold halves 15, 17 and respective cavities 15a, 17a arranged in an array.

The elastomer sheet 16 is preferably formed of one or more elastomeric materials (i.e., one or more of the elastomeric materials described above) in a partially cured stage. The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In another embodiment, the process conditions are 160 to 165° C. and about 50 kg/cm$^2$ for about 15 minutes. In another embodiment, the process conditions are 160 to 175° C. and 40 to 70 kg/cm² for about 8 minutes. As such, the elastomer sheet 16 is essentially an elastomer preform. The elastomer sheet 16 has a first surface 19 and an opposing second surface 21.

Figure 1B:
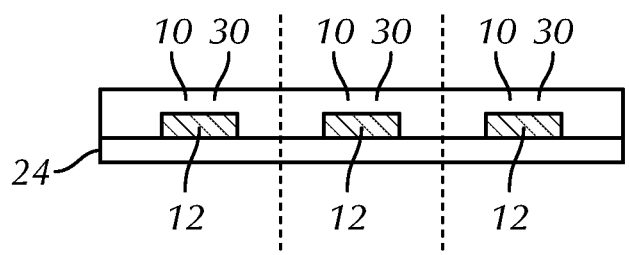

In the embodiment of FIGS. 1A-1B, the bottom surface of the mold cavity 17a of the lower mold half 17 defines a planar surface 23. The planar surface 23 also corresponds to the interior bottom surface of the lower mold half 17. The elastomer sheet 16 includes at least one electronic device 12 arranged or embedded therein. More particularly, the electronic device 12 is positioned within the elastomer sheet 16 such that an exposed or distal surface 12a of the electronic device 12 is flush with the second surface 21. In a preferred embodiment, the elastomer sheet 16 comprises a plurality of electronic devices 12 arranged in an array that corresponds to the array of mold cavities 15a, 17a.

In the embodiment of FIGS. 1A-1B, the elastomer sheet 16 further comprises a protective or barrier film 24 on the side of the second surface 21. The protective film 24 has a first surface 26 and an opposing second surface 28. The protective film 24 is provided so as to cover the exposed surface 12a of each electronic device 12, such that the first surface 26 of the protective film 24 is in direct contact with the exposed surface 12a of each electronic device 12. It will be understood that the protective film 24 may be provided only in the areas of the electronic devices 12 or so as to cover the entire second surface 21 of the elastomer sheet 16.

In the manufacturing method according to the embodiment of FIGS. 1A-1B, the elastomer sheet 16 is positioned over the lower mold half 17, such that the position of each electronic device 12 aligns with the position of a respective open mold cavity 17a. In the assembled position, the second surface 28 of the protective film 24 is in contact, and more particularly, direct contact with the planar surface 23. Each electronic device 12 is preferably held in place within the mold cavity 17a by vacuum assist. The assembly is then subjected to compression molding to fully cure the elastomeric material. More particularly, the mold 14 is closed such that each upper mold half 15 covers each respective lower mold half 17, and heat and pressure are applied to cause the elastomeric material of the elastomer sheet 16 to flow, thereby forcing the flowing elastomeric material into contact with all areas of each mold cavity 15a, 17a until the elastomeric material has cured to form the medical component 10.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

The resulting cured form includes one electronic device 12 per each mold part. Each resulting medical component 10 comprises an electronic device 12 fully encapsulated by the cured elastomeric material 30 and the protective film 24. The protective film 24 may be any polymer or ceramic film that would enable an electrical or optical path to the electronic device 12, but still provide barrier properties for encapsulation of the electronic device 12. In a preferred embodiment, the protective film 24 is a fluoropolymer film. Preferably, the fluoropolymer film 24 is provided on the surface of the medical component 10 which is configured to contact the pharmaceutical medicament (i.e., the interface or contact surface).

Fluoropolymers are readily known in the art and a detailed description of them is not necessary for a complete understanding of the present invention. Exemplary fluoropolymers include, but are not limited to, polytetrafluoroethylene (PTFE), homopolymers and copolymers of tetrafluoroethylene (TFE), perfluoroalkoxy polymer resin (PFA), copolymers of hexafluoropropylene and tetrafluoroethylene, polyethylenetetrafluoroethylene (PETFE), polyvinyl fluoride (PVF), fluorinated ethylenepropylene copolymers (FEP), polyethylenechlorotrifluoroethylene (PECTFE), polyvinylidene fluoride (PVDF), polychlorotrifluoroethylene (PCTFE), and derivatives thereof. Preferably, the protective film 24 is formed of FluoroTec®.

In the embodiment of FIGS. 2A-2E, the bottom surface 23 of the cavity 17a of each lower mold half 17 is recessed so as to be spaced apart from the elastomer sheet 16 in the assembled position. As such, during compression molding, the elastomeric material of the elastomer sheet 16 is able to flow into the space between the sheet 16 and the bottom surface 23, such that the electronic device 12 is fully encapsulated by the elastomeric material. As such, in the embodiments of FIGS. 2A-2E, the elastomer sheet 16 need not include the protective film 24.

Figure 2A:
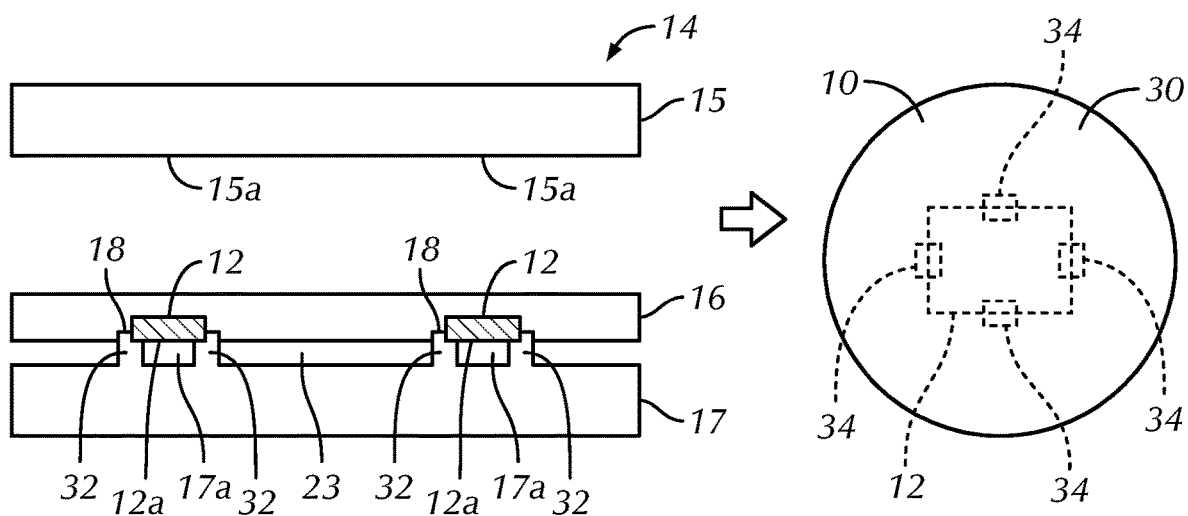
FIGS. 2A-2E illustrate methods of manufacturing a medical component in a one-step molding process according to other preferred embodiments of the present invention.

In the embodiment of FIG. 2A, each lower mold half 17 includes at least one protrusion 32, and more preferably a plurality of protrusions 32, for holding the electronic device 12 in place within the mold cavity 17a during the compression molding process, for example, to keep the electronic device 12 centered. More particularly, the plurality of protrusions 32 form a pedestal 18 upon which the elastomer sheet 16, and more particularly the electronic device 12, rests during compression molding, such that the exposed surface 12a of the electronic device 12 is spaced apart from the bottom surface 23 of the cavity 17a. As such, during compression molding, the electronic device 12 is held securely in place and the elastomeric material may flow into the space between the electronic device 12 and the bottom surface 23, such that the electronic device 12 is fully encapsulated by the elastomeric material in the finished medical component 10. As a result of the interaction between the pedestal 18 and the elastomer sheet 16 during the compression molding process, the finished medical component 10 may include a plurality of indentations or voids 34 in positions corresponding to the location of the distal ends of the protrusions 32 of the pedestal 18.

Figure 2E:
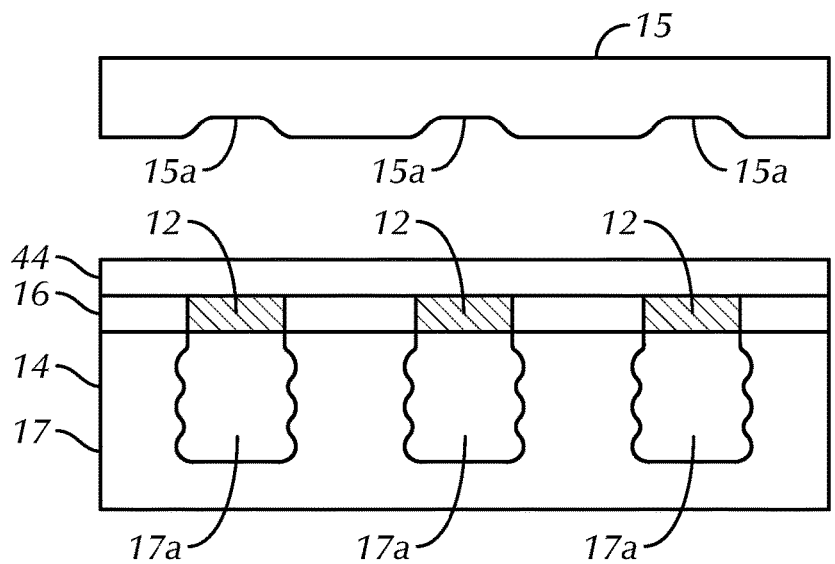
Figure 2B:
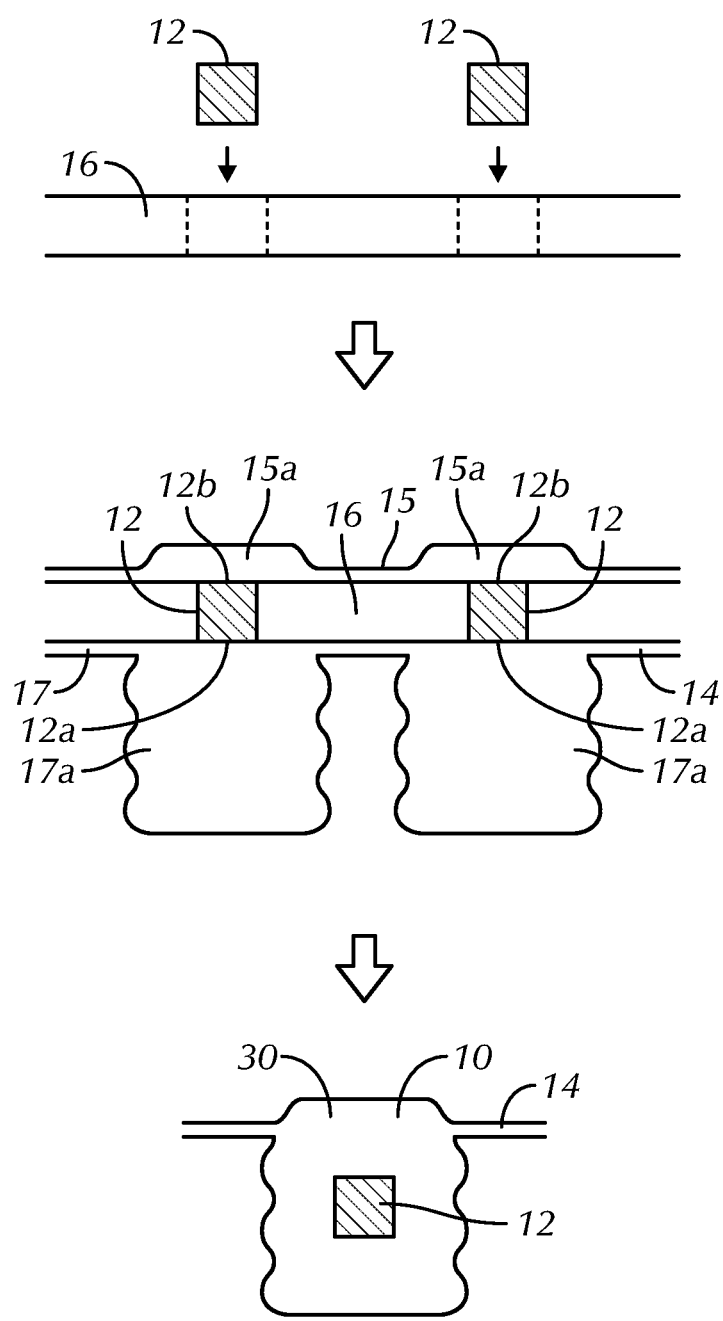

In the embodiment of FIG. 2B, the plurality of electronic devices 12 are embedded in the elastomer sheet 16, such that both the opposing distal and proximal surfaces 12a, 12b of the device 12 are exposed. The open cavities 15a, 17a of the mold halves 15, 17 are recessed in the respective walls of the mold halves 15, 17, such that during compression molding, the elastomeric material flows all around the electronic device 12, thereby ensuring that the electronic device 12 is fully encapsulated by the elastomeric material in the finished medical component 10.

In one variation, shown in FIG. 2E, the elastomeric sheet 16 is subjected to freezing temperatures (i.e. is frozen) before being positioned in the mold 14. This enables the sheet 16 to better hold its shape for a portion of the cure cycle and also allows for superior control in the placement of the encapsulated electronic devices 12 during the one-step molding process. The frozen elastomer sheet 16 is then positioned over the lower mold half 17, such that the position of each electronic device 12 aligns with the position of a respective open mold cavity 17a. The bottom surface of the cavity 17a of each lower mold half 17 is recessed so as to be spaced apart from the elastomer sheet 16 in the assembled position.

Next, a second elastomer sheet 44 is positioned over the frozen elastomer sheet 16. However, the second elastomer sheet 44 has not been frozen. Thus, during the molding process (e.g., compression molding), the elastomeric material of the second sheet 44 flows faster than that of the frozen sheet 16, allowing for better control of the alignment of the electronic devices 12 during the compression molding. The elastomeric material of both elastomer sheets 16, 44 is able to flow into the spaces of each open mold cavity 15a, 17a, such that each electronic device 12 is fully encapsulated by the elastomeric material. It will be understood that the first and second sheets 16, 44 may be formed of the same elastomeric material or different elastomeric materials.

The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

Figure 2C:
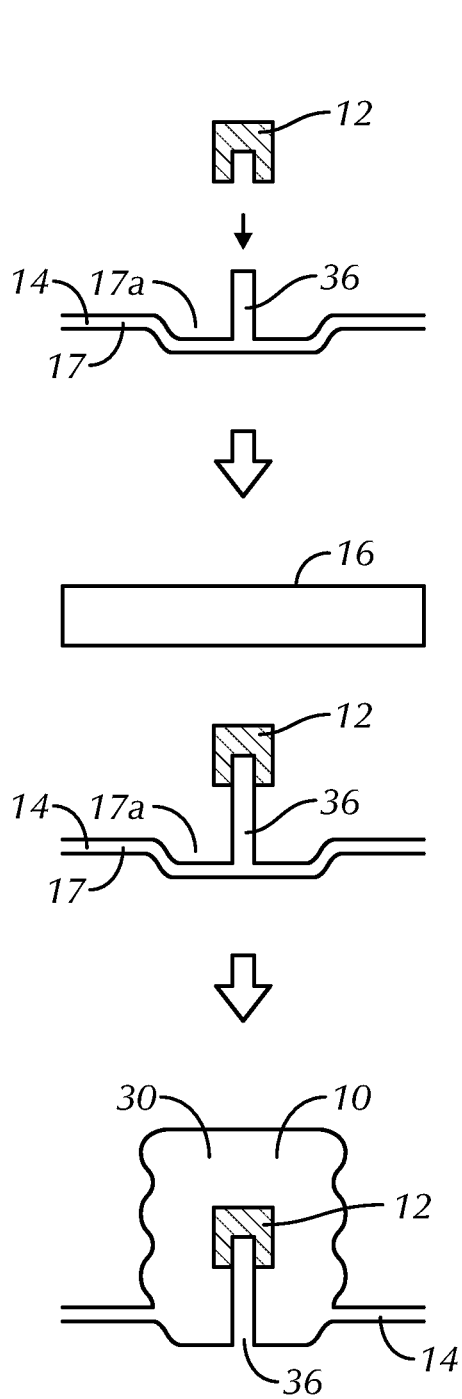

In the embodiment of FIG. 2C, the lower mold half 17 includes a protrusion 36 that mates with a corresponding indentation 38 formed in the electronic device 12, in order to hold the electronic device 12 in position during compression molding. The protrusion 36 is thus an alignment pin. In another embodiment, the protrusion 36 and the indentation 38 may be provided with mating threads. Again, the open cavities 15a, 17a of the mold halves 15, 17 are recessed in the respective walls of the mold halves 15, 17, such that during compression molding, the elastomeric material flows all around the electronic device 12, thereby ensuring that the electronic device 12 is fully encapsulated by the elastomeric material in the finished medical component 10.

Figure 2D:
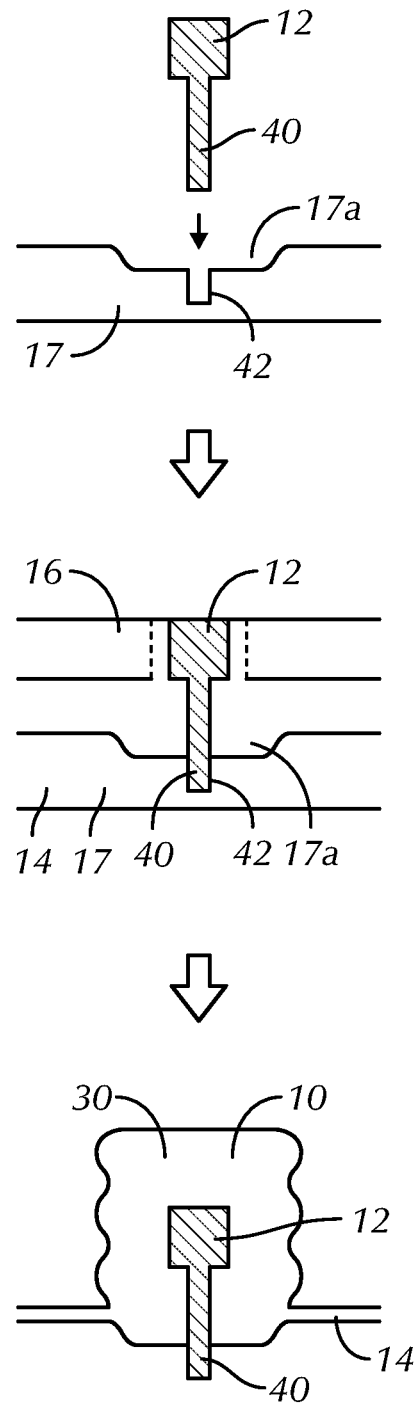

FIG. 2D depicts an embodiment in which the electronic device 12 includes a protrusion 40 that mates with a corresponding indentation 42 formed in the wall of the lower mold half 17. The body of the electronic device 12 is embedded within the elastomer sheet 16, similar to FIG. 2B, while the protrusion 40 extends outwardly away from the sheet 16. In another embodiment, the protrusion 40 and the indentation 42 may be provided with mating threads. Again, the open cavities 15a, 17a of the mold halves 15, 17 are recessed in the respective walls of the mold halves 15, 17, such that during compression molding, the elastomeric material flows all around the electronic device 12, thereby ensuring that the electronic device 12 is fully encapsulated by the elastomeric material in the finished medical component 10.

Referring to FIGS. 3A-3H, there is shown an embodiment of a method of manufacturing the medical component 10 utilizing an elastomer tube 116 in a one-step molding process. The molding process may be any known molding process (e.g., compression molding, injection molding and the like). The elastomer tube 116 is preferably formed of one or more elastomeric materials (i.e., one or more of the elastomeric materials described above) in an uncured or partially cured (i.e., semi-cured) state. The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

The elastomer tube 116 is essentially an elastomer preform. The elastomer tube 116 is generally cylindrical with a hollow interior 123, and has a first end 119 and an opposing second end 121. The portion of the tube 116 including the first end 119 is hereinafter referred to as a first half of the tube 116 and the portion of the tube 116 including the second end 121 is hereinafter referred to as a second half of the tube 116.

Figure 3E:
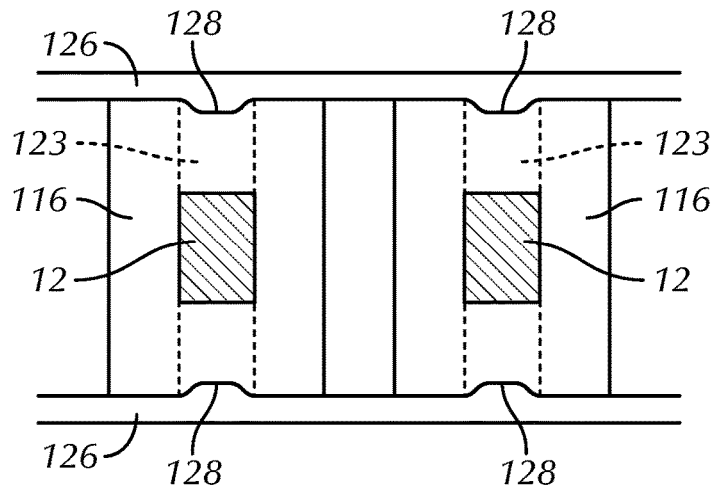
Figure 3F:
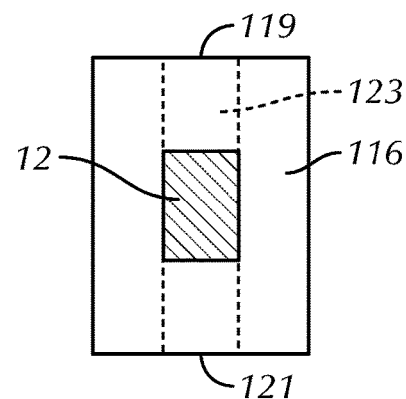

After the uncured or semi-cured elastomer tube 116 is formed, one or more electronic devices 12 is positioned within the hollow interior 123 of the tube 116. Next, one of various processes may be carried out to secure the electronic device 12 in place. For example, as shown in FIG. 3C, both the first and second halves of the tube 116 may be crimped or pinched together while the elastomeric material is still soft, pliable and tacky so as to maintain the electronic device 12 in place. Alternatively, as shown in FIG. 3D, extruded elastomeric rods or plugs 124 may be positioned in the hollow interior 123 in the first and second halves (i.e., on either side of the electronic device 12) to secure the electronic device 12 in place. Alternatively, as shown in FIG. 3E, preformed elastomeric sheets 126, each of which includes one or more protrusions 128, may be positioned on either end 119, 121 of the tube 116, such that the protrusions 128 are received within the hollow interior 123 of the tube 116, thereby securing the electronic device 12 in place. Alternatively, no further processes are necessary, as shown in FIG. 3F, if the electronic device 12 has already sufficiently secured itself within the hollow interior 123 (e.g., due to its size). It will be understood by those skill in the art that a combination of the aforementioned processes of FIGS. 3C-3F may be carried out. For example, the process of FIG. 3C may be used on the first half of the tube 116, while the process of FIG. 3D is used on the second half of the tube 116.

Figure 3G:
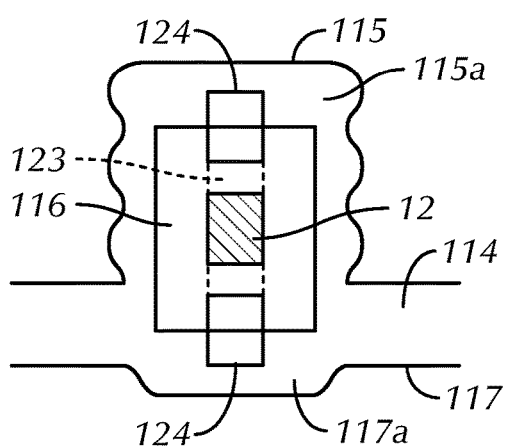
Figure 3H:
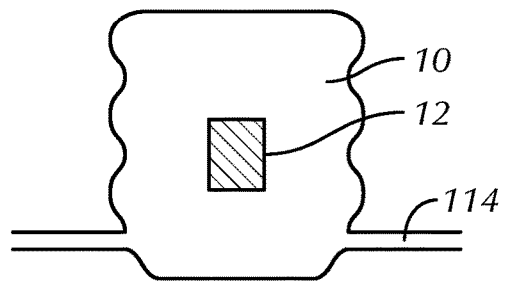

Finally, as shown in FIGS. 3G-3H, the uncured or semi-cured elastomeric tube 116 with the electronic device 12 secured therein is placed within a mold 114 and heat and pressure are applied to cause the elastomeric material of the elastomer tube 116 to flow, and the flowing elastomeric material fills any voids (i.e., in the hollow interior 123) while maintaining the center of the electronic device 12 (see FIG. 3H). The molding process is carried out under predetermined time, heat and pressure conditions, until the elastomeric material has cured to form the medical component 10.

The mold 114 includes an upper mold half 115 having an open cavity 115a and a lower mold half 117 having an open cavity 117a. Each cavity 115a, 117a is preferably an open heated mold cavity 115. In a preferred embodiment, the mold 114 includes a plurality of upper and lower mold halves 115, 117 and respective cavities 115a, 117a arranged in an array. As such, a plurality of semi-cured elastomeric tubes 116 with electronic devices 12 secured therein may be simultaneously compression molded to form the medical components 10.

The process conditions for this molding step are 120 to 310° C. and about 40 to 350 kg/cm$^2$ for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Figure 4A:
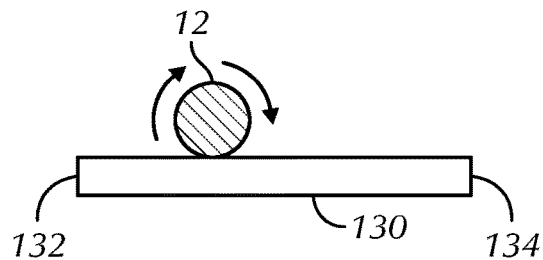
FIGS. 4A-4C schematically illustrate a method of manufacturing a medical component in a one-step molding process according to another preferred embodiment of the present invention.
Figure 4B:
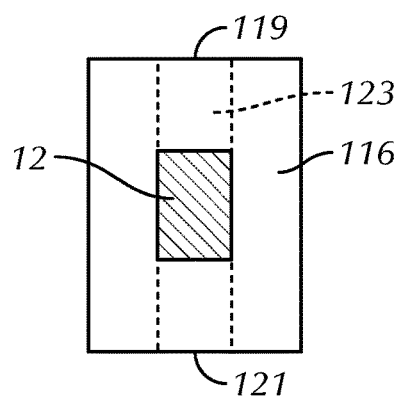
Figure 4C:
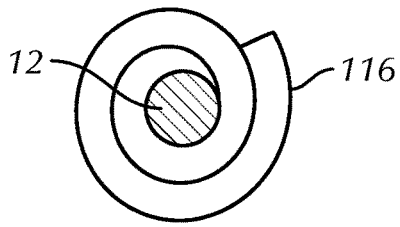

Referring to FIGS. 4A-4C, there are shown alternative embodiments for preparing the uncured or semi-cured elastomeric tube 116 and electronic device 12 assembly. Specifically, referring to FIG. 4A, an uncured or semi-cured elastomeric sheet 130 may be formed in a molding step/process under predetermined time, heat and pressure conditions. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

The sheet 130 is a generally planar and flat sheet having a first end 132 and an opposing second end 134. The electronic device 12 is placed on the flat surface of the sheet 130 proximate the first end 132, and more particularly proximate a geometric center of the first end 132. Then, the first end 132 of the sheet 130 is rolled over the electronic device 12 and continues to be rolled toward the second end 134. As such, the sheet 130 is wrapped around the electronic device 12, thereby forming the uncured or semi-cured elastomer tube 116 having an electronic device 12 positioned within a center of the hollow interior 123 of the tube 116, as shown in FIGS. 4B-4C. Next, the tube 116 and electronic device 12 are subjected to the securing and molding processes described above with respect to FIGS. 3A-3H in order to form the medical component 10.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Figure 5A:
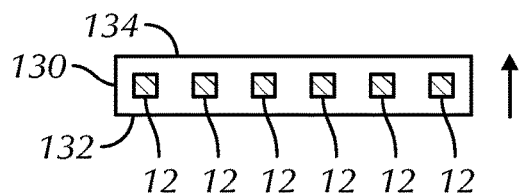
FIGS. 5A-5C schematically illustrate a method of manufacturing a medical component in a one-step molding process according to another preferred embodiment of the present invention.
Figure 5B:
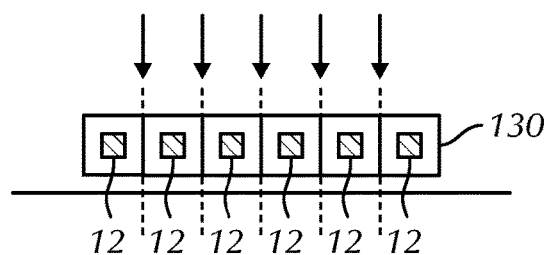
Figure 5C:
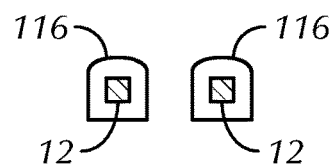

Alternatively, as shown in FIGS. 5A-5C, multiple tubes 116 may be formed simultaneously. Specifically, a plurality of electronic devices 12 are placed on the surface of the semi-cured elastomeric sheet 130 proximate the first end 132 at spaced-apart intervals (see FIG. 5A). Next, the sheet 130 is rolled over and wrapped around the electronic devices 12 in the same manner as described herein with respect to FIG. 4A. Next, referring to FIGS. 5B-5C, the sheet 130 is cut at the intervals separating the electronic devices 12, thereby forming a plurality of semi-cured elastomer tubes 116, each tube 116 having an electronic device 12 positioned within a center of its hollow interior 123. Finally, each tube 116 and electronic device 12 is subjected to the securing and molding processes described above with respect to FIGS. 3A-3H under the aforementioned time, heat and pressure conditions, in order to form a plurality of medical components 10.

Figure 6:
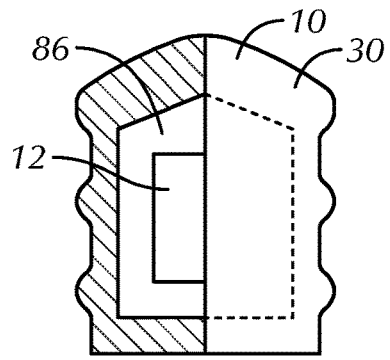
FIG. 6 illustrates a medical component including an electronic device embedded therein according to another preferred embodiment of the present invention.
Figure 7:
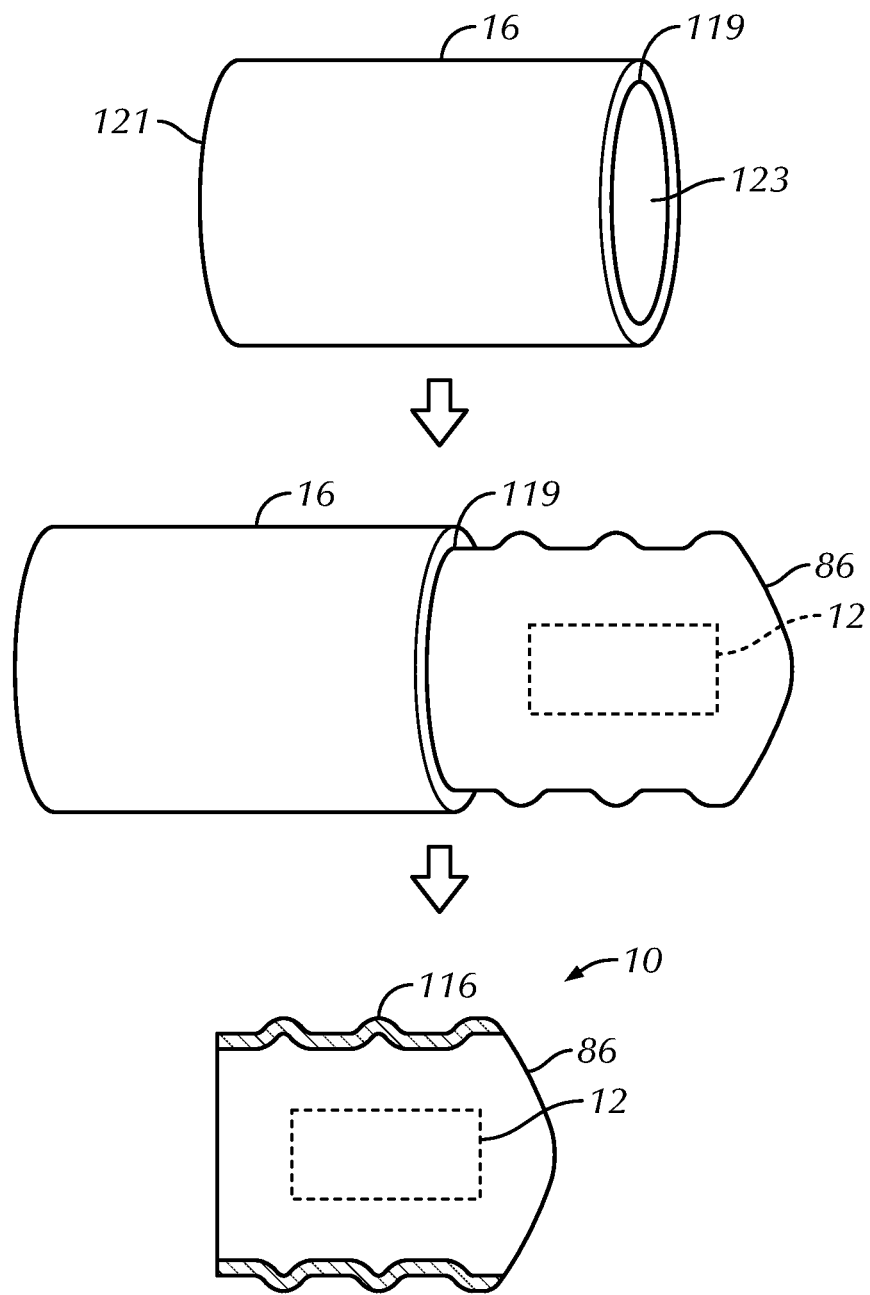
FIG. 7 schematically illustrate a method of manufacturing a medical component according to another preferred embodiment of the present invention.
Figure 8:
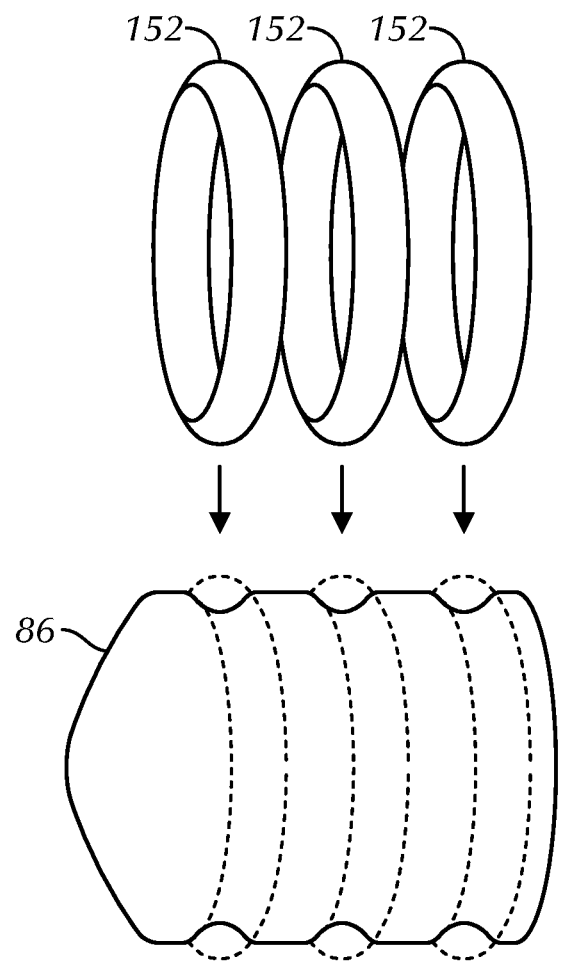
FIG. 8 schematically illustrate a method of manufacturing a medical component according to another preferred embodiment of the present invention.

Referring to FIGS. 6-8, there are shown further embodiments of a method of manufacturing the medical component 10 in a one-step molding process (e.g., compression molding, injection molding, overmolding and the like). Specifically, the electronic device 12 is initially embedded within a form or receptacle 86 formed of a temperature resistant and resilient material. More particularly, the form 86 is preferably formed of a thermally stable material. For example, the form 86 may be formed of materials including, but not limited to, a ceramic material, including but not limited to alumina or silicates (e.g., quartz, porcelain or glass); a metallic material including but not limited to stainless steel, titanium, aluminum and/or anodized aluminum; or a polymer material including, but not limited to polyamides, fluoropolymers including but not limited to polytetrafluoroethylene (PTFE) or glass filed PTFE, or a polyaryletherketone (PAEK) including but not limited to polyetherketoneketone (PEKK), polyetherketone (PEK), polyetherketoneetherketoneketone (PEKEKK) and polyether ether ketone (PEEK). In one embodiment, the form 86 may comprise insulated materials, such as foam or aerogel for thermal insulation or a high temperature resistant polymer for electrical isolation of the electronic device 12. Such a material would have various advantages. For example, in the case of providing thermal insulation, cryogenic storage could be used to minimize the time the electronic device 12 is exposed to high temperature. Also, a mechanically robust form 86 is preferred, such that particularly fragile or sensitive electrical devices 12, such as microelectromechanical systems or shock/acceleration sensors, may be used.

Preferably, the form 86 is of a size and shape that corresponds to the desired size and shape of the medical component 10 to be formed.

Next, in one embodiment, as shown in FIG. 6, the form 86 provided with the electronic circuit 12 is placed in a mold and the elastomeric material 30 is overmolded onto the form 86, under predetermined time, heat and pressure conditions, in order to form the medical component 10 comprising the elastomeric material 30. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

In one variation, for example where the form 86 is formed of a metallic material, the mold may be provided with a magnetic material (not shown) to facilitate accurate positioning and placement of the form 86 during molding.

In another embodiment, as shown in FIG. 7, an uncured or semi-cured elastomeric tube 116, and more particularly an uncured or semi-cured monolithic elastomeric tube 116, as described above, is formed and the form 86 provided with the electronic circuit 12 is inserted into the hollow interior 123 of the tube 116. More particularly, the tube 116 is stretched over the exterior surface of the form 86 and is mechanically formed onto the form 86. Subsequently, the assembly is subjected to the application of heat and pressure to cure and shrink-wrap the elastomeric material of the tube 116 onto the form 86. For example, a bladder type molding process may be employed to thermoform the elastomeric material of the tube 116 around the hard body of the form 86 and to provide a sufficiently smooth surface for sealability.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Alternatively, a process may be employed wherein the elastomeric material of the uncured or semi-cured elastomeric tube 116 is compressed and simultaneously rolled against a smooth surface or wheel to impart specific surface characteristics.

In one variation of the embodiment of FIG. 7, sealing elements (not shown), such as O-rings, may be utilized during the heating step, in order to ensure that the elastomeric material of the uncured or semi-cured elastomeric tube 116 is completely sealed onto the form 86. In one embodiment, the elastomeric material of the tube 116 is hermetically sealed onto the form 86 so as to provide additional barrier properties by fully enclosing any impurities associated with the material used to form the form 86 in which the electronic device 12 is embedded.

In one embodiment, as shown in FIG. 8, instead of using the elastomeric material 30 or uncured or semi-cured elastomeric tube 116, a plurality of sealing elements 152, such as O-rings, are utilized. The form 86 is generally the same as that of FIGS. 6-7. However, disposed around the form 86 are a plurality of generally equally, axially spaced, and radially extending circumferential rings 152, rather than the elastomeric material 30 or uncured or semi-cured elastomeric tube 116 of the previously-described embodiments of the present invention. The assembly is then subjected to a compression molding process to form the medical component 10. Compression molding is carried out for bonding, as needed. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

In another embodiment (not shown), disposed around the form 86 is a thin chemically resistant covering surrounded by the plurality of generally equally, axially spaced, and radially extending circumferential rings 152. The covering may be molded separately and applied to the form 86 or may be directly applied to and molded with the form 86 during molding thereof to enable compatibility with drug product contact. The cover may be formed of any chemically resistant or impervious material, including but not limited to a fluoropolymer (see above examples) or other inert plastic material which lacks the necessary elastomeric qualities for sealing, including but not limited to ethylene tetrafluoroethylene (ETFE), PTFE, perfluoroalkoxy alkanes (PFA), polyvinylidene fluoride (PVDF) and the like. The assembly is then subjected to the above-described compression molding process, wherein the O-rings 152 and cover can be completely cured along with the form 86.

Figure 9A:
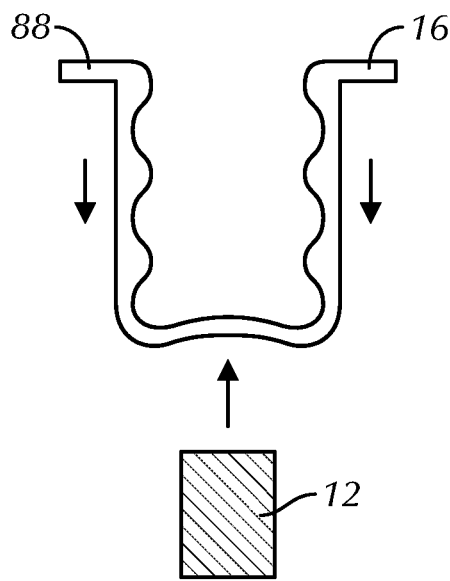
FIGS. 9A-9C illustrate a method of manufacturing a medical component in a one-step molding process according to another preferred embodiment of the present invention.
Figure 9B:
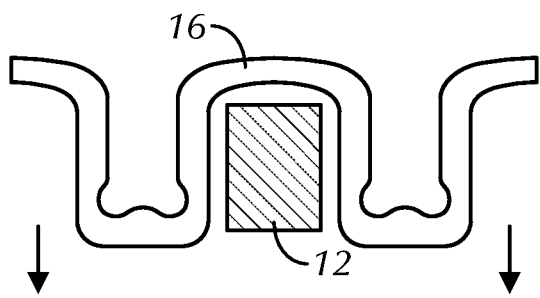
Figure 9C:
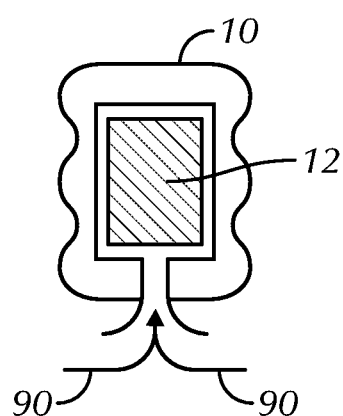

Referring to FIGS. 9A-9C, there is shown another embodiment of a method of manufacturing the medical component 10 in a one-step molding process under predetermined time, heat and pressure conditions. First, an elastomer sheet 16 comprising the elastomeric material is formed. The elastomer sheet 16 may be in a fully cured state, or in a partially or semi-cured state. Next, the elastomer sheet 16 is molded in an inverted shape 88 (i.e., inside out) by any known molding process (e.g., compression molding, injection molding and the like), under predetermined time, heat and pressure conditions. More particularly, the elastomeric material is molded into a shape that is the inverse of the shape of the medical component 10 to be formed. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Next, as shown in FIG. 9B, inversely molded article 88 is contacted with the electronic device 12, and inverted and rolled over the body of the electronic device 12 so as to encapsulate the electronic device 12. The article 88 is then shaped and stretched as necessary to achieve the desired shape and form of the medical component 10. More particularly, the inversely molded article 88 is thermoformed into the shape of the medical component 10. Also, as shown in FIG. 9C, in the end component 10, the trim edges 90 of the elastomer are enclosed, such that the external trim edges that result from conventional molding processes are eliminated. The time, heat and pressure for the thermoforming process will depend upon various factors, such as the specific elastomeric material being used.

Referring to FIGS. 10A-11B, there are shown other embodiments of methods of manufacturing the medical component 10 in a bladder molding process under predetermined time, heat and pressure conditions. The mold 14 is similar to that described above with respect to the process of FIG. 2E.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Figure 10A:
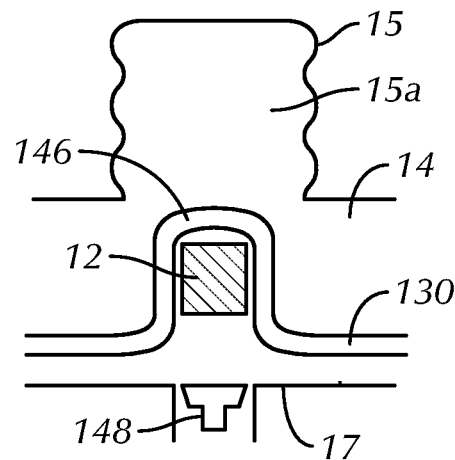
FIGS. 10A-10C schematically illustrate a method of manufacturing a medical component in a one-step molding process according to a further preferred embodiment of the present invention.
Figure 10B:
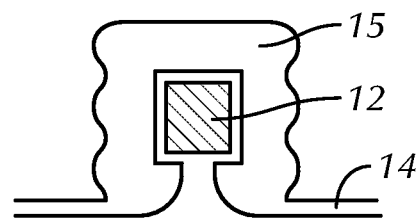
Figure 10C:
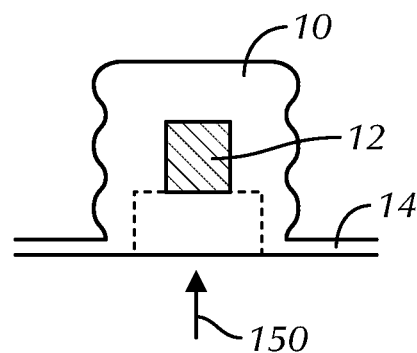
Figure 13A:
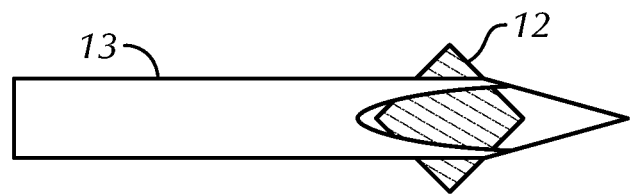
FIGS. 13A-13C illustrate different configurations of a push rod or needle provided with an electronic device for use in the method shown in FIGS. 12A-12B and 14-16.
Figure 13B:
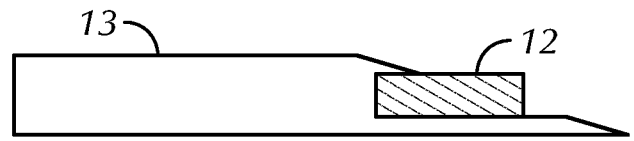
Figure 13C:
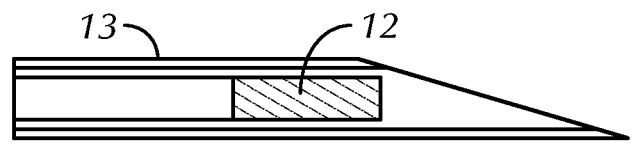

Specifically, referring to FIGS. 10A-10C, in the method of this embodiment, an uncured or partially cured elastomeric sheet 130 includes one or more dimples or recesses 146. Each dimple 146 is configured to receive an electronic device 12. As such, a preform is formed by inserting an electronic devices 12 into each dimple 146 of the uncured or partially cured elastomeric sheet 130. The preform is then arranged in the mold 14. Subsequently, air pressure is applied by an air valve 148 from one side of the mold 14 to force the elastomer sheet 130 and electronic devices 12 into the opposing mold cavity 15a (see FIGS. 10A-10B). The elastomeric material is stretched (e.g., by thermoforming) to the final shape and dimensions of the medical component 10 and then set or cured by the application of heat. Finally, additional elastomeric material 150 may be injected into the mold 14 to fill any voids in the medical component 10 (see FIG. 10C). The later-injected elastomeric material 150 may be the same as or different from the material of the elastomer sheet 130.

Referring to FIGS. 11A-11B, in an alternative embodiment, external pressure is applied to compress and form the elastomer sheet 130 into the medical component 10. Specifically, the preform of the elastomer sheet 130 with an electronic device 12 arranged in each dimple 146 is positioned in the mold 14, such that each dimple 146 is positioned within one of the cavities (e.g., cavity 15a), as shown in FIG. 11A. Next, the bladder mold 14 is inflated so as to apply external pressure and heat on the elastomer sheet 130 to form the elastomeric material into the shape and dimensions of the medical component 10, as shown in FIG. 11B.

Referring to FIGS. 12A-14, there is shown another embodiment of a method of manufacturing the medical component 10 in a one-step molding process under predetermined time, heat and pressure conditions. Specifically, the medical component 10 is molded in any desired shape, preferably by a conventional one-step compression molding process. However, it will be understood that any known molding process may be utilized (e.g., insert molding, injection molding and the like). In FIGS. 12A-12B, the medical component 10 is shown as a piston for a syringe, cartridge or vial.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Figure 14:
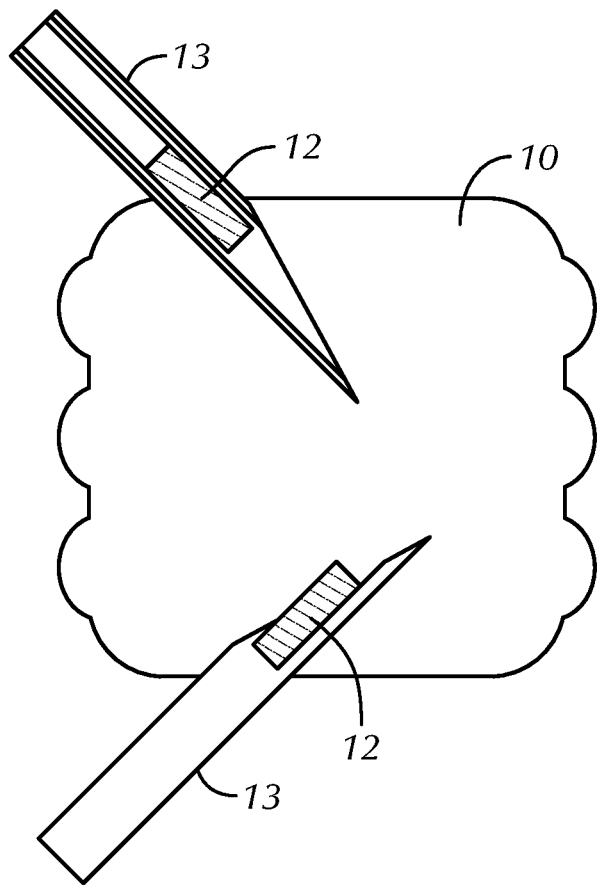
FIG. 14 schematically illustrates a method of embedding an electronic device in a medical component using the push rod or needle shown in FIGS. 13A-13C in accordance with a preferred embodiment of the present invention.

Next, one or more electronic devices 12 may be inserted or injected into the molded medical component 10 by any known technique, such that the one or more electronic devices 12 are embedded in the medical component 10 at the desired location(s). For example, a pushing rod or needle 13 including the electronic device 12 arranged therein (including but not limited to any of the configurations shown in FIGS. 13A-13C) may be used to inject the electronic device 12 into the medical component 10, as shown in FIG. 14. For example, the electronic device(s) 12 may be embedded in the medical component 10 just below a distal surface thereof (e.g., the surface configured to contact the pharmaceutical drug to be delivered to a patient via the medical device for light and/or temperature measurements) or near a lateral surface thereof (e.g., for easy communication with an external sensor). By this method, the location of the electronic device(s) can be easily tailored to any desired location. The electronic device 12 is held in place by the elasticity of the elastomer itself.

Figure 15:
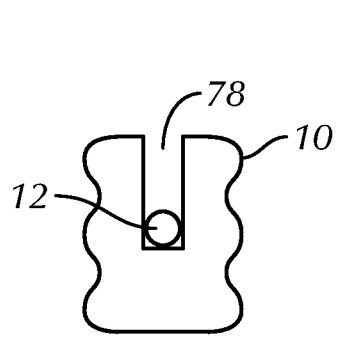
FIG. 15 is a schematic of a method of manufacturing a medical component in a one-step molding process according to another preferred embodiment of the present invention.

Alternatively, as shown in FIG. 15, one or more pilot holes 78 may be formed in the molded medical component 10 and the electronic device 12 is then inserted into the body of the medical component 10 through the pilot hole 78.

Figure 17A:
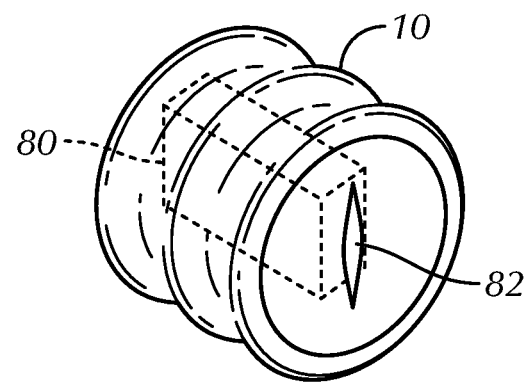
FIGS. 17A-17C illustrate medical components having a notch of various configurations according to another preferred embodiment of the present invention.
Figure 17B:
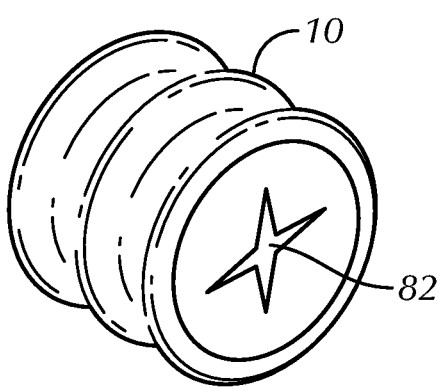
Figure 17C:
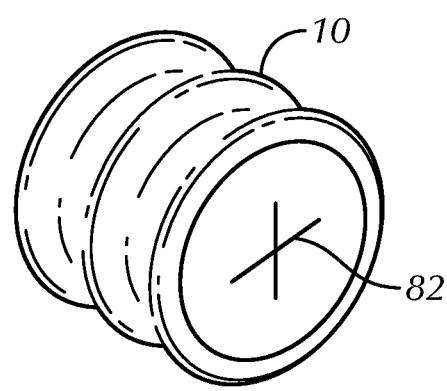

In another embodiment, as shown in FIG. 17A-17C, the medical component 10 may be molded, under the process conditions discussed above, so as to already include one or more cavities 80, each of which is configured to receive one or more electronic devices 12. At the entry of each cavity 80, and particularly in a surface of the molded component, a notch 82 is preferably provided to facilitate insertion of the electronic device 12 into the cavity 80. The notch 82 may have any known form. For example, notch 82 may be a biconvex opening, a Bite Valve™, a plurality of slits, and the like. After the electronic device 12 is inserted into the cavity 80, a piston rod may also be inserted through the same notch 82 and into the cavity 80.

Alternatively, the cavity 80 and notch 82 may be formed while the elastomer is in only a partially cured form, the electronic device 12 is then positioned in the cavity 80 in the partially cured body, and the partially cured body is then compression molded to cure the elastomer to form the medical component 10 and the notch 82 is closed by compression. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Figure 16:
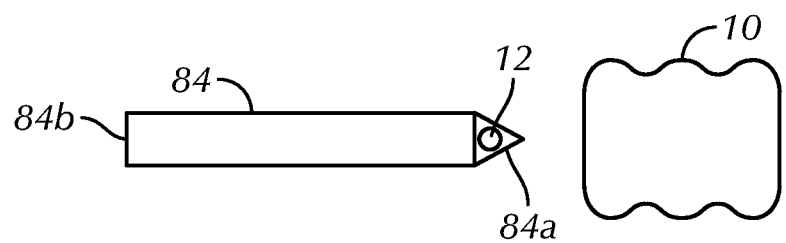
FIG. 16 is a schematic of a method of manufacturing a medical component in a one-step molding process according to another preferred embodiment of the present invention.

In another embodiment, as shown in FIG. 16, after the piston 10 has been molded, under any of the process conditions discussed above, the electronic device 12 may be inserted or embedded therein via a piston rod 84. More particularly, the piston rod 84 has a first end 84a formed as a spike and an opposing second end 84b. The spiked first end 84a is provided with an electronic device 12 either embedded therein or securely or permanently attached thereto. Beginning with the spiked first end 84a, the piston rod 84 is then inserted into the molded component 10. The molded component 10 may optionally have a cavity 80 and notch 82 as discussed above with reference to FIGS. 17A-17C.

The piercing spike 84a could then remain attached to the actuating rod 84 for power transmission and/or communication with the electronic device 12. The elimination of wireless communications prevents the possibility of interference, allows for greater power transmission with lower losses, and makes tampering/spoofing of signals more difficult. The piercing spike may be made of any known material, such as stainless steel or an injection molded plastic.

Referring to FIGS. 18A-18C, 19A-19C and 21A-21C, there are shown further embodiments of methods of manufacturing the medical component 10 in a two-step molding process. In FIGS. 18A-18C, 19A-19C and 21A-21C, the medical component 10 is depicted as a piston for exemplary purposes, but it will be understood that all of the methods discussed herein could be used to form any medical component.

Figure 18C:
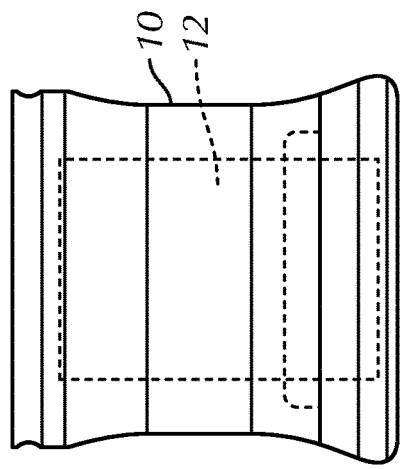
FIGS. 18A-18C illustrate a method of manufacturing a medical component in a two-step molding process according to another preferred embodiment of the present invention.
Figure 18B:
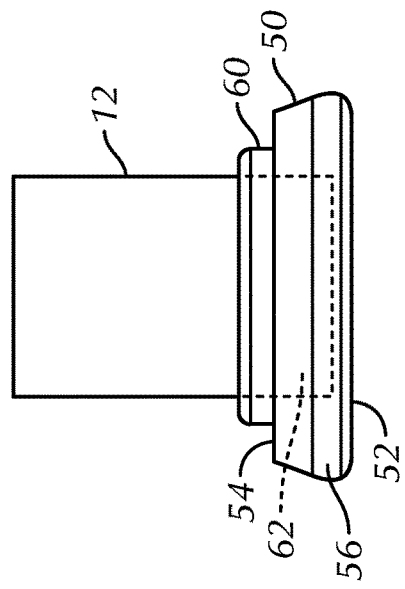
Figure 18A:
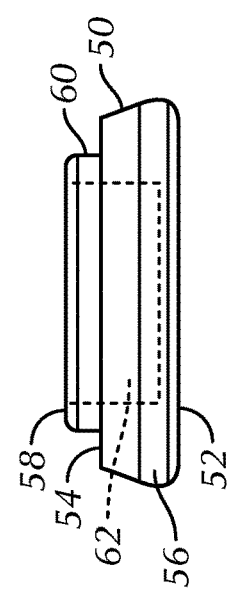
Figure 22A:
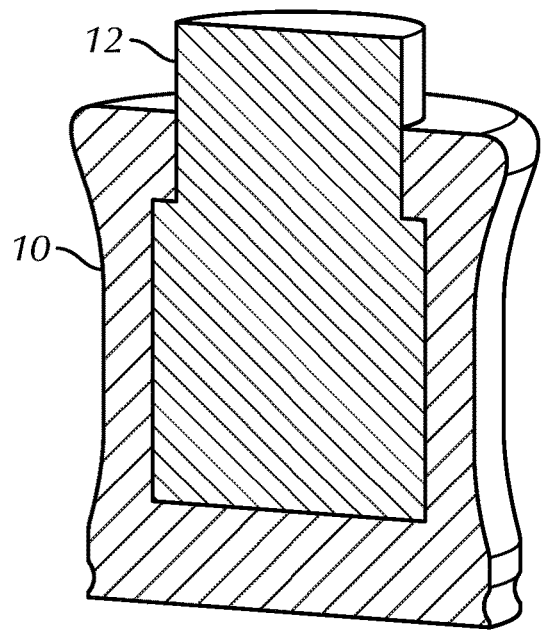
FIGS. 22A-22D show various medical components manufactured by the method shown in FIGS. 21A-21D.
Figure 22B:
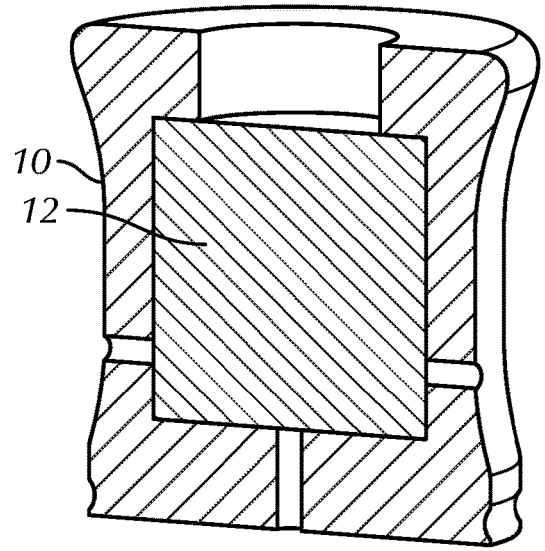
Figure 22C:
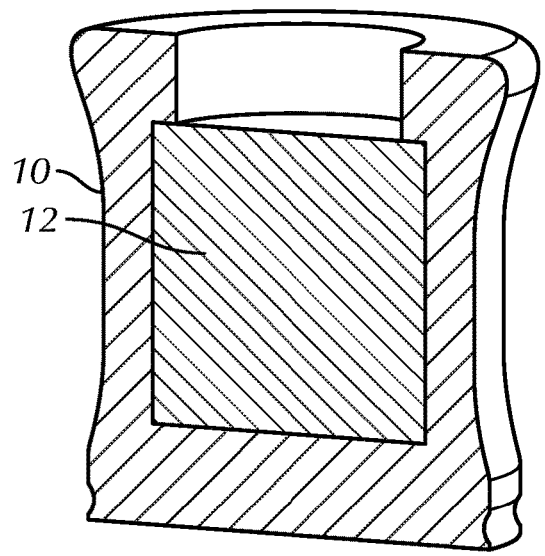
Figure 22D:
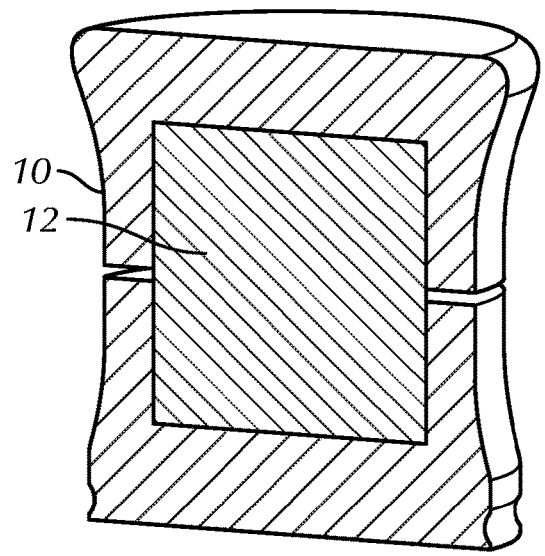

Referring to FIGS. 18A-18C, the method comprises forming a first member or base member 50 by molding of an elastomeric material (e.g., either a thermoset elastomer or a thermoplastic elastomer). It will be understood that the first member 50 may have any suitable shape which corresponds to the shape of the medical component 10 to be formed. However, as FIGS. 18A-18C relate to a piston 10, the first member 50 has a generally cylindrical shape. Preferably, the first member 50 defines the drug contact end of the piston 10.

The first member 50 preferably has a closed base wall 52, an open top end 54, and a sidewall 56 extending therebetween. The closed base wall 52, open top end 54, and an exterior sidewall 56 define an interior 58 of the first member 50. The interior 58 preferably includes an inner sidewall 60 surrounding a recess 62. The recess 62 is sized and shaped to receive a portion of the electronic device 12 therein.

In order to manufacture the medical component 10 according to the embodiment of FIGS. 18A-18C, the first member 50 is first formed by any known molding method (e.g., compression molding, insert molding, injection molding and the like) in a partially cured state. The process conditions for this molding step are 120 to 310° C. or higher and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

Then, as shown in FIG. 18B, the electronic device 12 is nested within the recess 62 of the first member 50, such that the electronic device 12 rests on or is proximate to the closed base wall 52. It will be understood that any known positioning mechanism or any of the positioning mechanisms described herein may be utilized to secure the electronic device 12 in place within the recess 62. For example, the electronic device 12 and the closed base wall 52 may be provided with corresponding (i.e., mating) protrusions (e.g., a threaded or smooth pin) and recesses or indentations, for purpose of enabling more robust placement and positioning of the electronic device 12.

Finally, in a second molding step, as shown in FIG. 18C, further elastomeric material is overmolded onto the assembled electronic device 12 and first member 50, and cured to form the finished medical component 10 in which the electronic device 12 is fully encapsulated by the elastomeric material. The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

Preferably, the overmolded elastomeric material is the same as the elastomeric material used to form the first member 50, but it will be understood that a different elastomeric material may be used.

In another embodiment, as shown in FIGS. 19A-19C and 20A-20B, instead of an overmolding process, a second member 66 is formed (e.g., molded under predetermined time, heat and pressure conditions as discussed herein) and assembled with the first member 50 to form the medical component 10. More particularly, the second member 66 is preferably molded from the same elastomeric material used to form the first member 50, but it will be understood that a different elastomeric material may be used. The second member 66 preferably has a closed base wall 68, an opposing open end 70, and a sidewall 72 extending therebetween.

The closed base wall 68, open top end 70, and the exterior sidewall 72 define an interior recess 74 of the second member 66. The interior recess 74 is preferably sized and shaped to receive the remaining portion of the electronic device 12 therein. The second member 66 preferably has a complementary shape and size to that of the first member 50 as necessary to achieve the desired shape and size of the medical component 10.

In order to manufacture the medical component 10 according to the embodiment of FIGS. 19A-20B, the first member 50 and second member 66 are first separately formed by any known molding method, under predetermined time, heat and pressure conditions as discussed herein, in partially cured states. The process conditions for these molding steps are 120 to 310° C. and about 40 to 350 kg/cm$^2$ for a few seconds to 30 minutes, more preferably about 120 to 70° C. and about 40 to 220 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

Then, the electronic device 12 is nested within the recess 62 of the first member 50, such that the electronic device 12 rests on or is proximate to the closed base wall 52. It will be understood that any known positioning mechanism or any of the positioning mechanisms described herein may be utilized to secure the electronic device 12 in place within the recess 62. Next, the second member 66 is assembled with the first member 50 in a mold, such that the open top ends 54, 70 contact each other at an interface 76 and the electronic device 12 is received within the recesses 62, 74 of the first and second members 50, 66.

Next, in accordance with one embodiment, the assembled first and second members 50, 66 are bonded or welded together by heating the entire assembly in the mold to fully cure the elastomeric material under predetermined time, heat and pressure conditions. The process conditions for this molding step are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm$^2$ for about 2 to 15 minutes. In one embodiment, the process conditions are 150 to 175° C. and 40 to 70 kg/cm$^2$ for about 10 minutes. In another embodiment, the process conditions are 160 to 165° C. and about 50 kg/cm$^2$ for about 15 minutes. In another embodiment, the process conditions are 160 to 175° C. and 40 to 70 kg/cm$^2$ for about 8 minutes.

Optionally, as shown in FIGS. 20A-20B, a layer of curable gum 92 may be placed at the interface 76 prior to the heating in order to facilitate bonding of the first and second members 50, 66. Such a process, utilizing pre-molded first and second members 50, 66, avoids the possibility of the viscous flow of the elastomer from damaging the electronic device 12 that would occur in, for example, a one-step overmolding process.

Alternatively, in accordance with another embodiment, a localized curing process may be implemented. More particularly, the first and second members 50, 66 may be initially molded in a fully cured state. The process conditions for these molding steps are 120 to 310° C. and about 40 to 350 kg/cm$^2$ for a few seconds to 30 minutes, more preferably about 120 to 220° C. and about 40 to 70 kg/cm$^2$ for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Next, the electronic device 12 and first and second members 50, 66 are assembled as discussed above, and bonded or welded together at the interface 76, optionally provided with the gum layer 92, by a directed energy source, such as, but not limited to, ultrasonic welding, microwave heating/curing, and laser heating/curing, that effects localized curing the elastomeric material and gum at the interface 76. The localized curing process protects the encapsulated electronic device 12 from being subjected to extreme conditions. The process conditions for this localized curing step is 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Referring to FIGS. 21A-21D, there is shown another embodiment of a method of manufacturing the medical component 10 in a two-step molding process. First, the first member 50 is molded as described herein with respect to FIGS. 18A-20B. Next, the body of the second member 66 is either overmolded onto the first member 50 (similar to the process of FIGS. 18A-18C) or separately formed and welded to the first member 50 (similarly to the process of FIGS. 19A-20B). The body of the second member 66 preferably includes a pocket or cavity 94 configured to receive the electronic device 12, and an opening 96, for example at a surface opposing to the drug contacting surface of the first body 50 or at a lateral surface, through which the electronic device 12 is inserted in order to be embedded in the cavity 94 within the medical component 10.

FIGS. 22A-22D show various embodiments of the structure and arrangement of the medical component 10 provided with an electronic device 12.

Figure 23A:
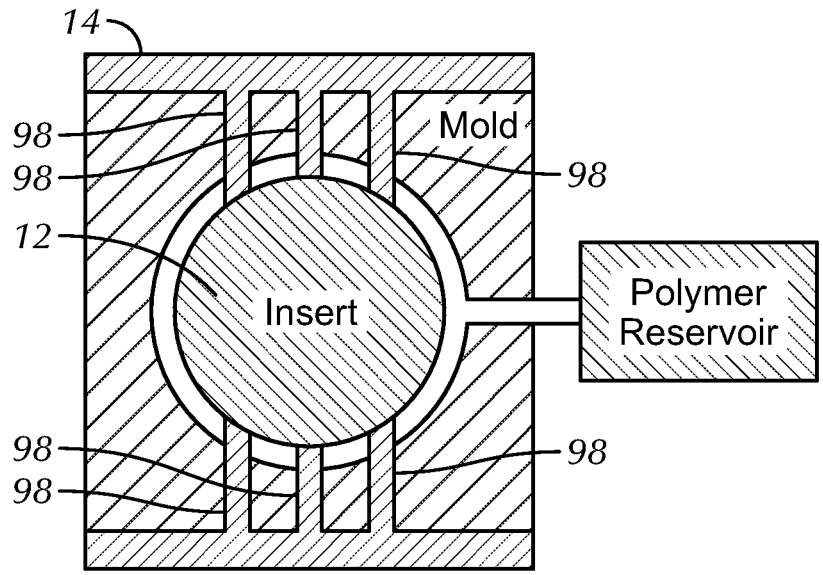
FIGS. 23A-23B illustrate a method of manufacturing a medical component in a one-step molding process according to another preferred embodiment of the present invention.
Figure 23B:
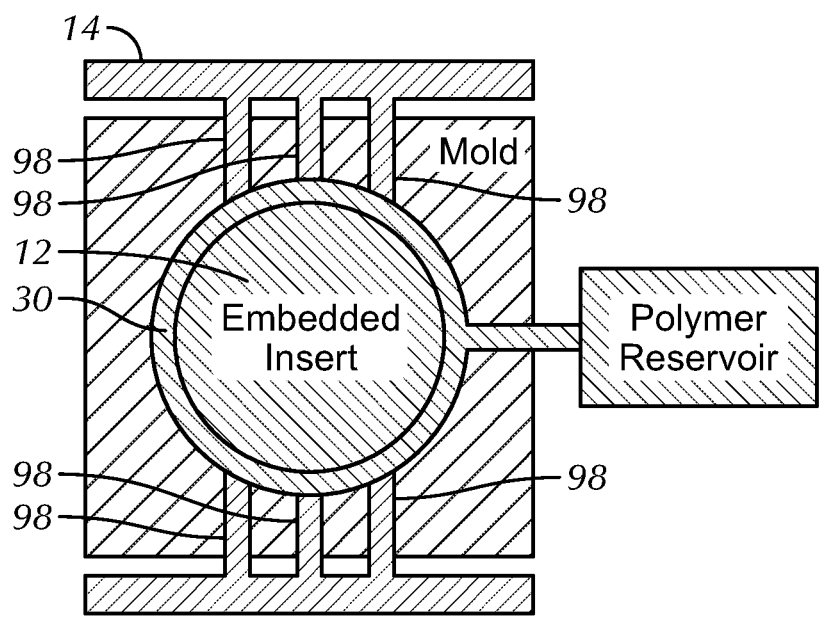

In any of the embodiments disclosed herein, retractable holding pins or protrusions 98 may be used to secure the electronic device 12 in position during the molding process (e.g., compression molding, injection molding and the like, preferably injection molding), as shown in FIGS. 23A-23B. Specifically, a plurality of holding pins 98 are initially used to center the electronic device 12 upon placement in a mold 14. Next, the molding process begins and elastomeric material 30 begins to surround the aligned electronic device 12. When the elastomeric material 30 sufficiently surrounds the aligned electronic device 12 (i.e., to the extent that the electronic device 12 will not be easily dislodged from its center), the holding pins 98 are retracted toward the mold 14 and away from the electronic device 12, thereby allowing the elastomeric material 30 to fully encapsulate the electronic device 12.

A fully encapsulated electronic device 12, as achieved by any of the methods described herein, has the benefit of being fully protected from its environment and would likely be capable of steam sterilization.

The electronic device or package 12, according to any of the embodiments described herein, may incorporate sensing technology, such as sensors to measure/detect the temperature of medical device/component itself or the surrounding environment, the pressure within the medical device, the differential pressure across the medical component 10 (e.g., the piston) which may occur, for example, by gas generation within the container due to drug breakdown, the capacitance for liquid level or the piston position, or light exposure for photosensitive drugs. The electronic device or package 12, according to any of the embodiments described herein, may also incorporate tracking technology, such as electronics to identify information encoded in an EEPROM or NFC chip. The device 12 may contain a serial number or expiration date, and may be traceable, for example, to determine whether or not a drug is under recall. The device 12 may also be used to confirm that the medical component 10 is an official product, rather than a third party grey market copy or other counterfeit. The device 12 may also be used, for example, by an RFID check to ensure that the medical component 10 is an appropriate delivery device for the drug to be dispensed. The device 12 may also be used to control the dispensing of the drug from the medical component 10 and to update inventory levels automatically.

The electronic device or package 12, according to any of the embodiments described herein, may also incorporate measurement technology, such as for measuring or detecting the location of a piston during use and/or the speed of delivery of the drug (e.g., by monitoring the piston rate of movement), or for providing feedback about when a piston reaches a pre-set dosage point (for example, the device 12 may be used to drive haptic feedback in the medical component 10). In cases where the piston 10 is a replaceable component, the electronic device 12 may be used to determine when the replacement should occur or if drug exposure should be limited. The electronic device 12 may also be used to detect tampering. For example, the device 12 may include a resistive foil whose value changes if it is punctured by a needle.

The electronic device or package 12, according to any of the embodiments described herein, may also incorporate various other types of technology. For example, the device 12 may incorporate muscle wire (flexinol or Shape Memory Actuator Wire) technology in the shape of a coil inside the rubber medical component 10 coupled to the electronic device 12. When a current flows throw the muscle wire, the muscle wire contracts. Such functionality could be used, for example, to tense/relax the piston 10, in order to make it easier or more difficult to move. The device 12 may also incorporate piezo technology (including, but not limited to, PVDF which is a piezoelectric material or a piezoelectric device) to agitate the drug contained in the medical component 10 prior to use. Another possible use of the electronic device 12 is to actuate induction heating to heat the drug contained in the medical component 10 prior to use, or to effect intentional spoiling of the drug if a tampering or misuse alarm is triggered or if a patient is attempting to dispense the drug after its expiration date. The electronic device 12 may also enable electrical contact between the piston 10 and the actuating rod to supply power to the piston electronics and confirm if the drug contained in the medical device is correct, monitor the date, etc.

The present invention may also be implemented to encapsulate other materials, besides an electronic device 12, inside of the medical component 10. For example, any of the methods described herein may be used to encapsulate or embed an incompressible material in the elastomeric body of the medical component 10 to change the mechanical properties of the medical component 10. Alternatively, any of the methods described herein may be used to encapsulate or embed a dense material in the elastomeric body of the medical component 10 to change the weight of the medical component 10, for example, for purposes of gravity or acceleration induced operation of the medical component 10. Alternatively, any of the methods described herein may be used to encapsulate or embed a magnet or a magnetic material in the elastomeric body of the medical component 10, such that the magnet or magnetic material is configured to interact with external sensors or magnetic packaging.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of manufacturing a medical component, the method comprising:
    preparing a first sheet of an elastomeric material;
    arranging at least one electronic device in the first sheet of elastomeric material to obtain an elastomeric preform;
    applying a protective film on a surface of the elastomeric preform, such that the protective film covers an exposed surface of the at least one electronic device;
    aligning the elastomeric preform covered by the protective film in a mold such that the at least one electronic device is received within an open cavity defined by the mold; and
    molding the elastomeric preform covered by the protective film to cure the elastomeric material and form the medical component having the at least one electronic device embedded therein.

2. The method of claim 1, wherein the protective film comprises an electrical or optical path to the at least one electrical device such that the protective film provides a barrier property for encapsulation of the at least one electrical device.

3. The method of claim 2, wherein the electrical or optical path is insulated by the protective film from a medicament.

4. The method of claim 2, wherein the electrical or optical path comprises an electrical contact through the protective film, such that the electrical contact engages with the exposed surface of the at least one electrical device.

5. The method of claim 2, wherein the protective film encapsulates the at least one electronic device, and the protective film is electrically conducive.

6. The method of claim 2, wherein a surface of the protective film covers an entire second surface of the first sheet of the elastomeric material.

7. The method of claim 1, wherein the protective film is a fluoropolymer film.

8. The method of claim 1, wherein the mold includes an upper mold half and a lower mold half defining the open cavity, a bottom surface of the open cavity of the lower mold half being recessed so as to be spaced apart from the elastomeric preform, such that during the molding, the elastomeric material of the elastomeric preform flows into a space between the elastomeric preform and the bottom surface to encapsulate the at least one electronic device by the elastomeric material.

9. The method of claim 1, wherein at least one of the mold or the elastomeric preform includes an element for facilitating positioning of the elastomeric preform and/or centering of the at least one electronic device during the molding.

10. The method of claim 1, further comprising
    at least partially freezing the elastomeric preform to form a partially frozen elastomeric preform;
    preparing a second sheet of elastomeric material;
    positioning the partially frozen elastomeric preform and the second sheet of elastomeric material in the mold, the mold having a lower half and an upper half, the first sheet being in direct contact with the lower half; and
    applying heat and pressure to the partially frozen elastomeric preform and the second sheet of elastomeric material in the mold to form the medical component having the at least one electronic device embedded therein.

11. The method of claim 1,
    wherein the first sheet of the elastomeric material is the form of a tube of an uncured or a partially cured elastomeric material, the tube having a first end, an opposing second end and a hollow interior extending between the first and second ends; and
    wherein the at least one electronic device is arranged in the hollow interior to form the elastomeric preform.

12. The method of claim 11, further comprising crimping the first end of the tube together and crimping the second end of the tube together prior to molding the elastomeric preform.

13. The method of claim 11, further comprising inserting a plug into each of the first and second ends of the tube after arranging the at least one electronic device therein.

14. The method of claim 1, wherein the protective film is a polymer or ceramic film.

* * * * *